(12) United States Patent
Lebedyeva et al.

(10) Patent No.: US 11,970,435 B2
(45) Date of Patent: Apr. 30, 2024

(54) TASTE-MODIFIED CREATINE SALTS, COMPOUNDS, COMPOSITIONS AND USES THEREOF

(71) Applicant: Augusta University Research Institute, Inc., Augusta, GA (US)

(72) Inventors: Iryna Lebedyeva, Augusta, GA (US); Christopher Klug, Aiken, SC (US)

(73) Assignee: AUGUSTA UNIVERSITY RESEARCH INSTITUTE, INC., Augusta, GA (US)

( * ) Notice: Subject to any disclaimer, the term of this patent is extended or adjusted under 35 U.S.C. 154(b) by 344 days.

(21) Appl. No.: 16/612,792

(22) PCT Filed: May 7, 2018

(86) PCT No.: PCT/US2018/031319
§ 371 (c)(1),
(2) Date: Nov. 12, 2019

(87) PCT Pub. No.: WO2018/208647
PCT Pub. Date: Nov. 15, 2018

(65) Prior Publication Data
US 2020/0148632 A1    May 14, 2020

Related U.S. Application Data

(60) Provisional application No. 62/505,179, filed on May 12, 2017.

(51) Int. Cl.
| | | |
|---|---|---|
| *C07C 279/14* | (2006.01) | |
| *A23L 27/00* | (2016.01) | |
| *A23L 33/175* | (2016.01) | |
| *C07D 291/06* | (2006.01) | |
| *C07J 31/00* | (2006.01) | |

(52) U.S. Cl.
CPC ........... *C07C 279/14* (2013.01); *A23L 27/84* (2016.08); *A23L 27/86* (2016.08); *A23L 33/175* (2016.08); *C07D 291/06* (2013.01); *C07J 31/006* (2013.01); *A23V 2002/00* (2013.01)

(58) Field of Classification Search
CPC .. C07C 279/14; A61K 31/221; A23K 20/142; A23L 27/86; A23L 27/84; A23L 33/175; A23V 2002/00; C07D 291/06; C07J 31/006
USPC ......................... 426/535, 534, 536, 537, 538
See application file for complete search history.

(56) References Cited

U.S. PATENT DOCUMENTS

| | | |
|---|---|---|
| 2002/0081360 A1 | 6/2002 | Burgard et al. |
| 2005/0194561 A1 | 9/2005 | Davis, Jr. |
| 2008/0124439 A1 | 5/2008 | Nuralam |
| 2008/0319076 A1 | 12/2008 | Kneller |
| 2015/0306051 A1 | 10/2015 | Miller et al. |

FOREIGN PATENT DOCUMENTS

| | | |
|---|---|---|
| WO | 0170238 A1 | 9/2001 |
| WO | 2017066787 A1 | 4/2017 |

OTHER PUBLICATIONS

Chenguang Wang et al., "Anion Exchange Reaction for Preparing Acesulfame Solid Forms", Crystal Growth and Design, 2018, 18, 4215-4219 http://pubs.acs.org/.

Jianhui Li et al., "Quinine Acesulfamates", Cryst. Growth Des. 2017, 17, 58-66, http://pubs.acs.org/.

*Primary Examiner* — Leslie A Wong
(74) *Attorney, Agent, or Firm* — PABST PATENT GROUP LLP

(57) ABSTRACT

Provided are embodiments of creatine and creatine ethyl ester (CEE) salts where the anion is an artificial (non-saccharide) taste-modifier. These compounds represent stable white non-hygroscopic solids or semisolids that can readily dissolve in water and buffer solutions. Synthesis of novel creatine salts using environmentally safe solvents such as ethanol resulted in the formation of products in quantitative yields with sodium or potassium chloride as a byproduct. The creatine and creatine alkyl eater derivative salts are stable sweet-tasting compounds that are more palatable to a consumer than creatine or derivatives thereof.

28 Claims, 3 Drawing Sheets

TASTE-MODIFIED CREATINE SALTS, COMPOUNDS, COMPOSITIONS AND USES THEREOF

CROSS-REFERENCE TO RELATED APPLICATIONS

This application is the 35 U.S.C. 371 national stage application of PCT Application No. PCT/US2018/031319, filed on May 7, 2018, where the PCT claims priority benefit of U.S. Provisional Patent Application Ser. No. 62/505,179 filed on May 12, 2017, and titled "TASTE-MODIFIED CREATINE SALTS, COMPOUNDS, COMPOSITIONS AND USES THEREOF" the entire disclosures of which are herein incorporated by reference in their entireties.

This application claims priority to and the benefit of U.S. Provisional Application 62/505,179 titled "TASTE-MODIFIED CREATINE SALTS, COMPOUNDS, COMPOSITIONS, AND USES THEREOF" filed May 12, 2017, the entire disclosure of which is incorporated herein by reference in its entirety.

TECHNICAL FIELD

The present disclosure is generally related to taste-modified salts of creatine and creatine derivatives and methods of making. The present disclosure is also generally related to dietary supplemental compositions containing taste-modified salts of creatine and creatine derivatives.

BACKGROUND

Daily update of dietary creatine and supplementation can lead to significant increases in skeletal muscle mass on resistance-trained human subjects (Hultman et al., (1985) *J. Appl. Physiol.* 81: 232-237; Cooper et al., (2012) *J. Int. Soc. Sports Nutrit.* 2012. 9: 1). It has been shown that creatine deficiency syndrome can lead to neurodevelopmental delay, seizures, and behavioral changes (Pacheva et al., (2016) *Ann. Clin. Lab. Sci.* 46: 557-561). Creatine can be used to treat such conditions as progressive muscle weakness (Kley et al., (2013) *Cochrane Database Syst. Rev.* Cd004760), facilitate the uptake of selective serotonin reuptake inhibitors (Lyoo et al., (2012) *Am. J. Psychiatry.* 169: 937-945), impact the influence of AMP kinase expression and activity in human skeletal muscle (Ingwall, J. S. (2002) *J. Mol. Cell Cardiol.* 34: 1111-1120), and it also improves brain performance (Rae et al., (2003) *Proc. Royal Soc. London B:* 270: 2147-2150). Creatine analogs have also been claimed to treat obesity (U.S. Pat. No. 5,998,457) and perform as antiviral compounds (U.S. Pat. No. 5,321,030). However, use of creatine as a food supplement to facilitate muscle growth among athletes has been the leading use for this compound (Rawson & Volek (2003) *J. Strength Conditioning Res.* 17: 822-831; Volek & Rawson (2004) *Nutrition* 20: 609-614; Lattavo et al., (2007) *Pediatric Clinics N. Am.* 54: 735-760).

Creatine monohydrate has been known for its low stability (Ganguly et al., (2003) *AAPS PharmSciTech.* 4), bitter taste (U.S. Pat. No. 5,886,040) and hygroscopic properties. This led to the development of many creatine salts (U.S. Pat. No. 5,886,040) and some creatine derivatives and special formulations (Hagebock et al., (2014) *Food Function* 5: 359-363).

Creatine is consumed by the body rapidly and undergoes intramolecular cyclization into creatinine and to maintain the high concentration of creatine, 2-5 g daily is the standard amount to intake (Kamber et al., (1999) *Med. Sci. Sports and Exercise* 31: 1763-1769; U.S. Pat. No. 5,773,473). Several formulations have been reported to improve creatine transport into skeletal muscles (U.S. Pat. Nos. 7,749,547 and 8,613,959).

Currently, the creatine salt market is presented with creatine monohydrate (U.S. Pat. No. 5,719,319), buffered creatine monohydrate (trademarked as Kre-Alkalyn®) (U.S. Pat. No. 6,399,661; US Patent Publication Nos. 20100056633 and 20110039928), creatine hydrochloride, (Bagchi et al., (2003) Nutrition and enhanced sports performance: Muscle building, endurance, and strength. Acad. Press), creatine magnesium chelate (Brilla et al., (2003) *Metabolism* 52: 1136-1140; U.S. Pat. No. 6,399,661), creatine malate (U.S. Pat. No. 5,973,199), creatine citrate (Jäger et al., (2008) *J. Int. Soc. Sports Nutrition* 5: 1), creatine nitrate (U.S. Pat. No. 8,569,369), creatine succinate (U.S. Pat. No. 7,226,947), creatine formate (U.S. Pat. No. 7,226,947), creatine gluconate (U.S. Pat. No. 7,226,947), creatine taurinate (U.S. Pat. No. 6,861,554), creatine pyroglutamate (U.S. Pat. No. 7,482,474), creatine pyruvate (U.S. Pat. No. 5,886,040), creatine glycinate (U.S. Pat. No. 7,511,173), and micronized creatine (Hezave et al., (2010) *J. Supercritical Fluids* 55: 316-324), creatinol-O-phosphate, creatine polyhydrate. For some of these multi-functional salts the formation of di- and tri-creatine salts is also possible.

Creatine derivatives are presented by creatine ethyl ester (CEE) (Gufford et al., (2013) *J. Dietary Supplements* 10: 241-251), creatine ethyl (and other alkyl groups) ester hydrochloride (U.S. Pat. Nos. 6,897,334 and 9,434,753) and creatine phosphate (Peeters et al., (1999) *J. Strength Conditioning Res.* 13: 3-9). Creatine N-acyl, or N,N-diacyl derivatives have recently been reported to improve solubility and increase stability (U.S. Pat. No. 9,114,150) and bioavailability of creatine (US Patent Publication No. 20150238453). However, some of these salts and derivatives have disadvantages in regard to taste, hygroscopicity, and the like.

SUMMARY

Briefly described, one aspect of the disclosure encompasses embodiments of a salt, or a solvate thereof, of creatine or a cationic derivative of creatine, and an anionic taste-modifier and can have the formula I:

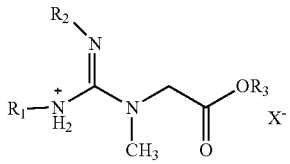

wherein $R_1$ and $R_2$ can each be independently an alkyl group or a hetaryl group and $R_3$ can be H or an alkyl group and X can be an anionic taste-modifier.

In some embodiments of this aspect of the disclosure, the creatine derivative can be a creatine alkyl ester cation.

In some embodiments of this aspect of the disclosure, R can be an alkyl group, or a monounsaturated alkyl having a $C_1$-$C_{16}$ chain.

In some embodiments of this aspect of the disclosure, R can be selected from the group consisting of a methyl group, an ethyl group, a propyl group, a butyl group, and a palmitoleate group.

In some embodiments of this aspect of the disclosure, the creatine alkyl ester cation can be a creatine ethyl ester (CEE) cation.

In some embodiments of this aspect of the disclosure, the anionic taste-modifier can be selected from the group consisting of: saccharinate, acesulfamate, taurocholate, neotamate, cyclamate, and steviolate, and anionic derivatives thereof.

In some embodiments of this aspect of the disclosure, the anionic taste-modifier can be a sweetener selected from saccharinate and acesulfamate.

In some embodiments of this aspect of the disclosure, the salt can be selected from the group consisting of:

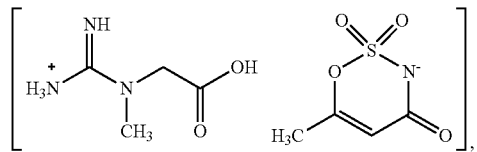

21a

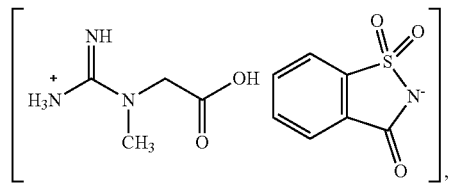

21b

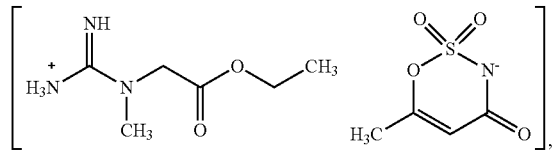

23a

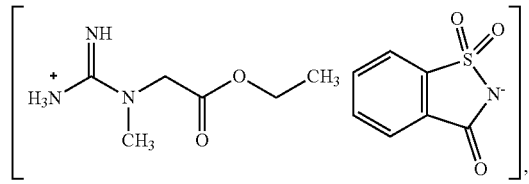

23b

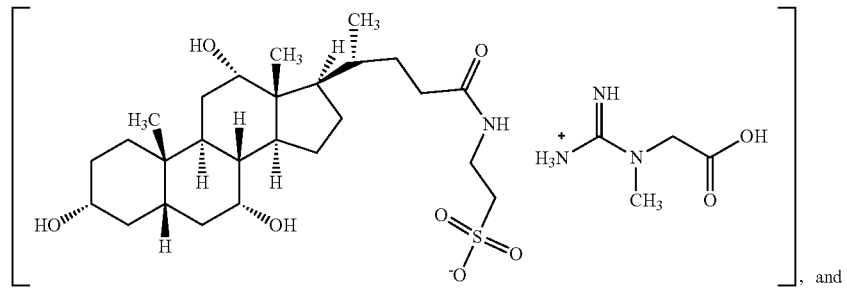

25

, and

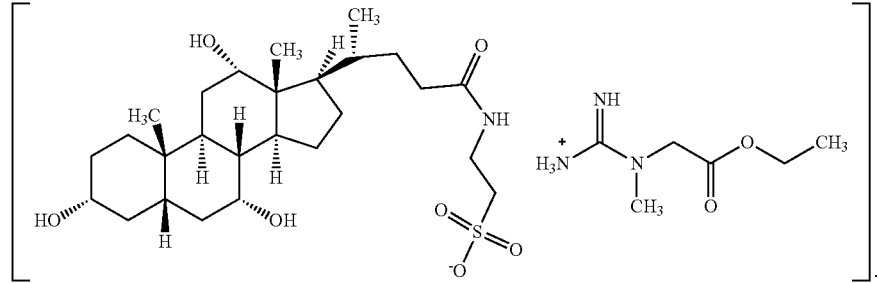

26

.

Another aspect of the disclosure encompasses embodiments of a composition comprising at least one mono- or poly-creatine salt or solvate thereof, wherein each salt or hydrate thereof consists of creatine or a cationic derivative of creatine, and an anionic taste-modifier and can have the formula I:

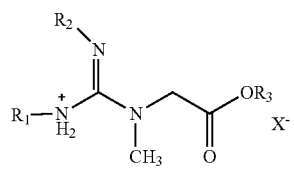

wherein $R_1$ and $R_2$ can each be independently an alkyl group or a hetaryl group and $R_3$ can be H or an alkyl group and X can be an anionic taste-modifier.

In some embodiments of this aspect of the disclosure, the creatine derivative can be a creatine alkyl ester cation.

In some embodiments of this aspect of the disclosure, R can be an alkyl group, or a monounsaturated alkyl having a $C_1$-$C_{16}$ chain.

In some embodiments of this aspect of the disclosure, R can be selected from the group consisting of a methyl group, an ethyl group, a propyl group, a butyl group, and a palmitoleate group.

In some embodiments of this aspect of the disclosure, the creatine alkyl ester cation can be a creatine ethyl ester (CEE) cation.

In some embodiments of this aspect of the disclosure, the anionic taste-modifier of each of the at least one of said salts can be selected from the group consisting of: saccharinate, acesulfamate, taurocholate, neotamate, cyclamate, and steviolate, and anionic derivatives thereof.

In some embodiments of this aspect of the disclosure, the anionic taste-modifier can be a sweetener selected from saccharinate and acesulfamate.

In some embodiments of this aspect of the disclosure, each of the at least one of said salts can be independently selected from the group consisting of:

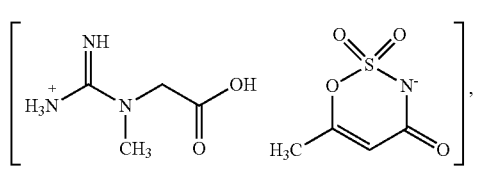
21a

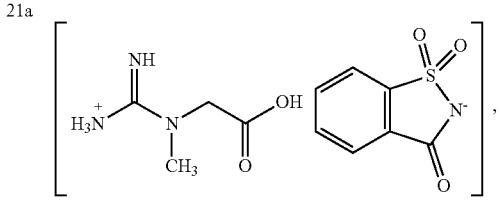
21b

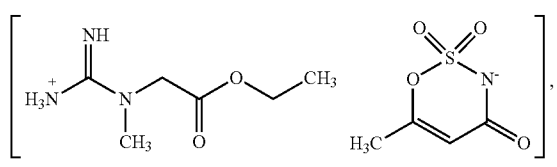
23a

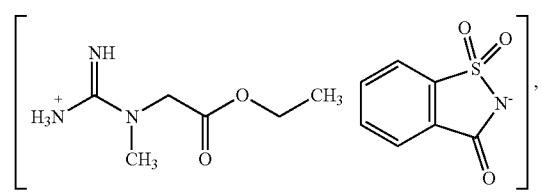
23b

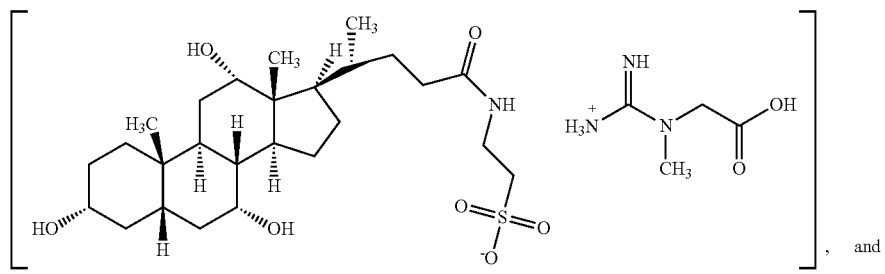
25

, and

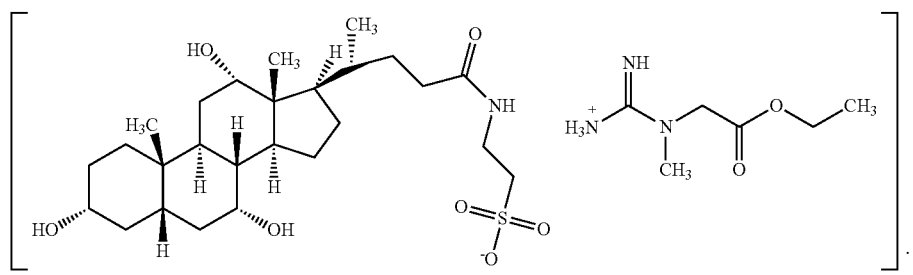
26

.

In some embodiments of this aspect of the disclosure, the composition can be a powder, an ionic liquid, or an oil.

In some embodiments of this aspect of the disclosure, the composition can further comprise an aqueous medium in an amount that does not result in dissociation of the creatine, or a cationic derivative of creatine, and the anionic taste-modifier. In some embodiments, the percent weight of the aqueous medium is from 0.001% to about 30%, from 0.001% to about 20%, 0.001% to about 10%, from 0.001% to about 5%, from 0.001% to about 2%, from 0.001% to about 1%, from 0.001% to about 0.5%, or from 0.001% to about 0.1%.

In some embodiments of this aspect of the disclosure, the creatine or a cationic derivative of creatine, and the anionic taste-modifier can be admixed with a non-aqueous medium.

In some embodiments of this aspect of the disclosure, the non-aqueous medium can be an edible oil or lipid.

In some embodiments of this aspect of the disclosure, the composition can be in a foodstuff or beverage formulated for consumption by a human or animal.

Still another aspect of the disclosure encompasses embodiments of a dietary supplement composition contained in a bulk package, wherein the dietary supplement composition is a powder, a non-aqueous oil, or a semi-solid, the bulk package containing the dietary supplement composition and, optionally, a measuring scoop sized to scoop an amount of the dietary supplement composition suitable for blending with a liquid to form a single serving of a beverage, the dietary supplement composition consisting essentially of at least one creatine salt or solvate thereof, wherein each salt or solvate thereof consists of creatine or a cationic derivative of creatine, and an anionic taste-modifier.

In some embodiments of this aspect of the disclosure, the cationic creatine derivative can be a creatine alkyl ester cation.

In some embodiments of this aspect of the disclosure, the creatine alkyl ester cation can be a creatine ethyl ester (CEE) cation.

In some embodiments of this aspect of the disclosure, the anionic taste-modifier of each of the at least one of said salts is selected from the group consisting of: saccharinate, acesulfamate, taurocholate, neotamate, cyclamate, and steviolate, and anionic derivatives thereof.

In some embodiments of this aspect of the disclosure, the anionic taste-modifier can be a sweetener selected from saccharinate and acesulfamate.

In some embodiments of this aspect of the disclosure, the at least one of said salts can be independently selected from the group consisting of:

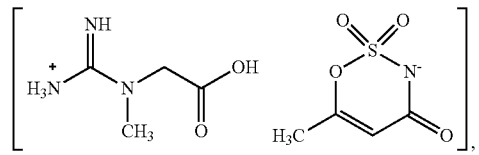

21a

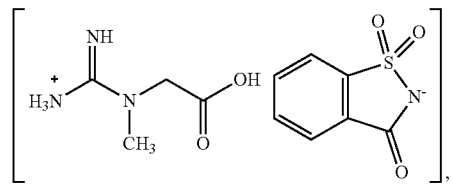

21b

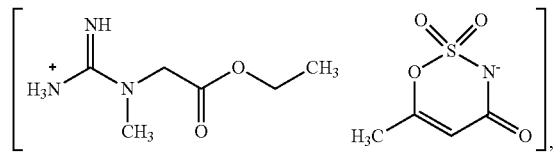

23a

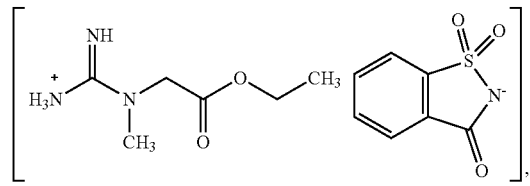

23b

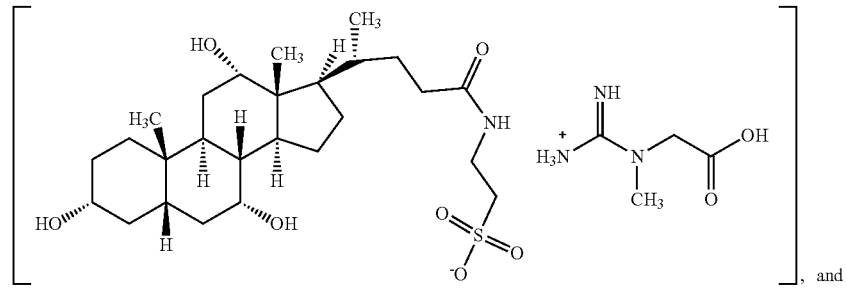

25

, and

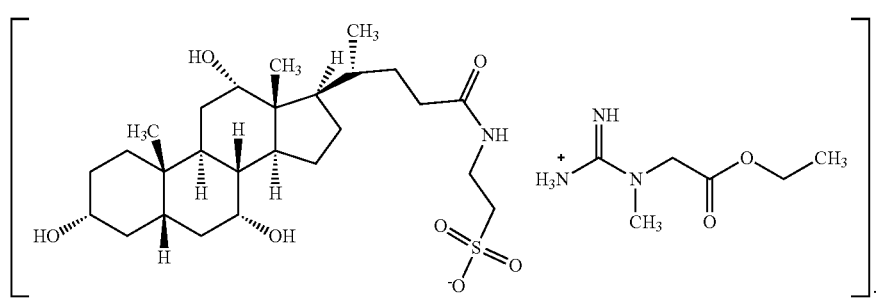

BRIEF DESCRIPTION OF THE DRAWINGS

Further aspects of the present disclosure will be more readily appreciated upon review of the detailed description of its various embodiments, described below, when taken in conjunction with the accompanying drawings.

DETAILED DESCRIPTION

Figure 1:
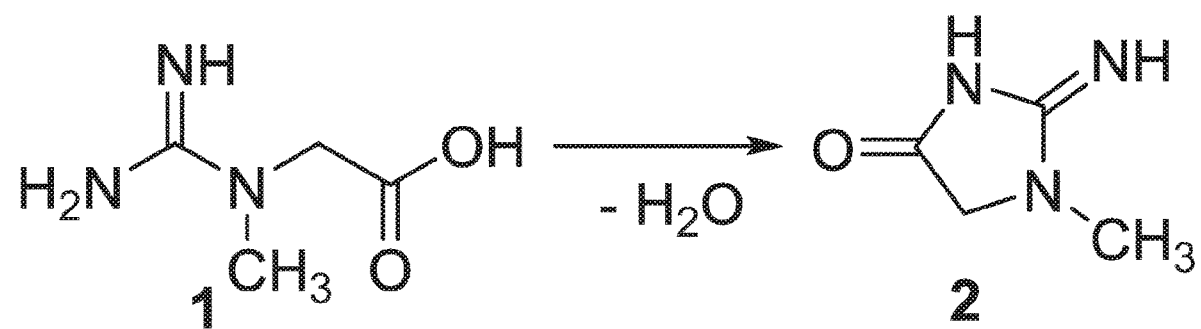
FIG. 1 illustrates the intramolecular cyclization of creatine into creatinine.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, food chemistry, nutrition, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein.

Prior to describing the various embodiments, the following definitions are provided and should be used unless otherwise indicated.

Definitions

The term "creatine" as used herein refers to 2-[carbamimidoyl(methyl)amino]acetic acid (alternatively N-carbamimidoyl-N-methylglycine; methylguanidoacetic acid) and is an amino acid produced naturally in the liver and kidneys and obtained from food such as meat and fish, Creatine can also be synthesized in the laboratory by several routes. Creatine functions as part of the cell's energy shuttle. The high energy phosphate group of adenosine triphosphate (ATP) is transferred to creatine to form phosphocreatine. This reaction is reversibly catalyzed by creatine kinase, also referred to as creatine phosphokinase. At sites of high energy usage, such as at the site of muscle contraction, creatine kinase transfers the high energy phosphate back from phosphocreatine to adenosine diphosphate (ADP) to reform ATP. This allows the cellular ATP/ADP ratio to remain stable within the cell, even if it is undergoing rapid energy fluctuations. Creatine kinase is typically located in cells that undergo high energy fluctuations. The presence of this energy shuttle keeps the ATP/ADP ratio high, which ensures that the free energy of ATP remains high and minimizes loss of adenosine nucleotides, which would cause cellular dysfunction.

Figure 2:
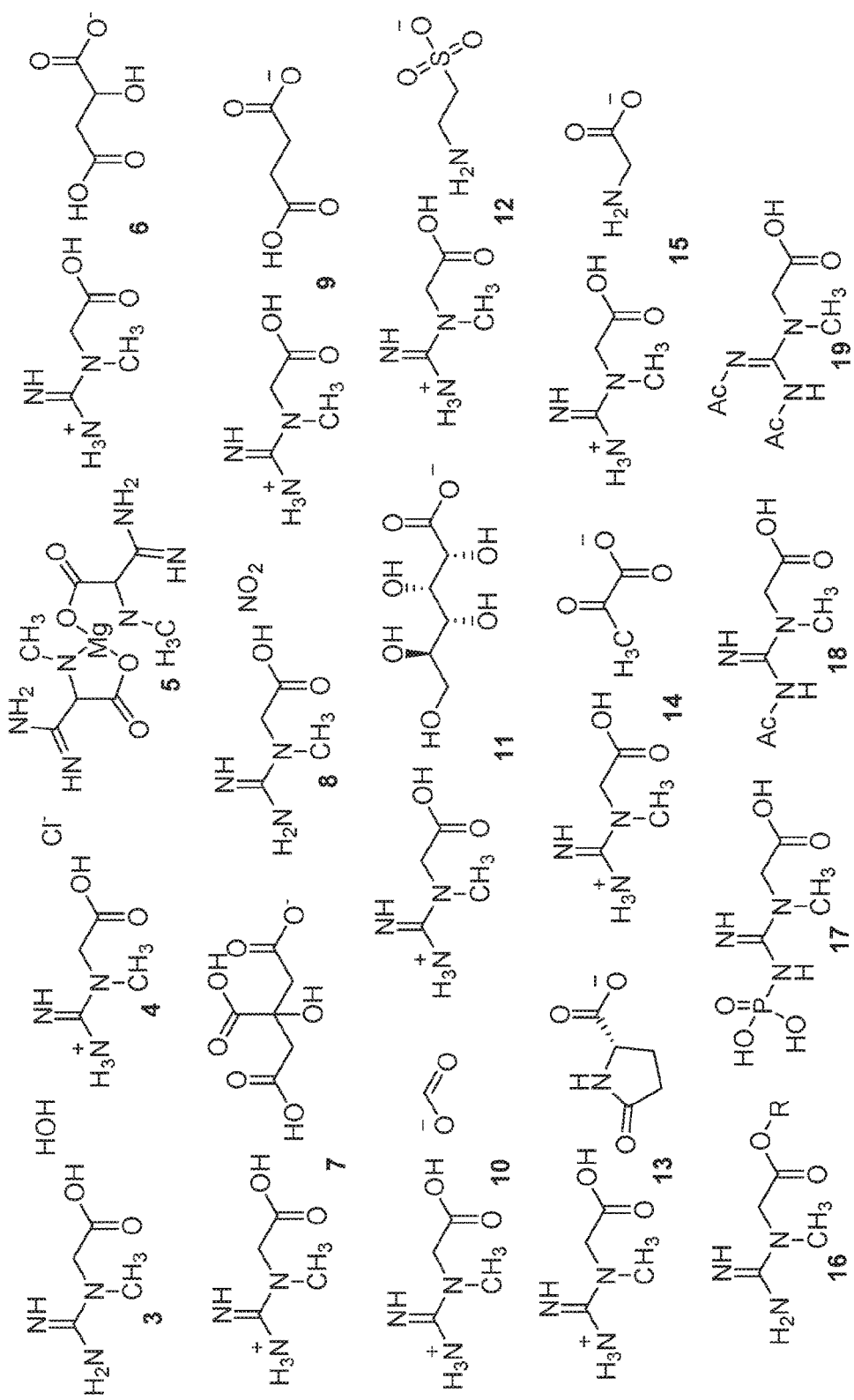
FIG. 2 illustrates prior art creatine salts 3-15 and derivatives 16-19.

The term "creatine" as used herein is further intended to include derivatives having alkyl groups or hetaryl groups such as, but not limited to, the creatine derivatives 17-19 as shown in FIG. 2.

The term "creatine alkyl ester (CAE)" as used herein refers to creatine or a derivative thereof having an alkyl ester group.

The term "creatine ethyl ester (CEE)" as used herein refers to ethyl N-(arninoiminomethyl)-N-rnethylglycine.

The term "taste-modifier" as used herein refers to an anion that, when in association with a cationic form of creatine or a derivative thereof, changes the perceived flavor or taste of an ingested food or beverage comprising creatine or a derivative. Creatine alone is perceived as bitter. Most advantageously an anionic taste-modifier can be a sweetener and, therefore, may mask totally or partially the bitter taste of creatine. Less advantageously, if desirable to increase the bitterness of a composition comprising creatine the anionic taste-modifier may be, for example, taurocholate.

The term "sweetener" as used herein refers to a substance, most commonly a sugar substitute (artificial sweetener), added to food to give it the basic taste of sweetness.

The term "saccharinate" as used herein refers to the anion derived from saccharine or from sodium (2H-1$\lambda$6,2-benzothiazol-1,1,3-trione).

The term "acesulfamate" as used herein refers to the anion derived from the salt potassium 6-methyl-2,2-dioxo-2H-1,2$\lambda^6$,3-oxathiazin-4-olate.

The term "taurocholate" as used herein refers to the anion derived from the sodium salt of taurocholic acid (2-{[(3$\alpha$,5$\beta$,7$\alpha$,12$\alpha$)-3,7,12-trihydroxy-24-oxocholan-24-yl]amino}ethanesulfonic acid).

The term "neotamate" as used herein refers to the anion derived from neotame ((3S)-3-(3,3-Dimethylbutylamino)-4-[[(2S)-1-methoxy-1-oxo-3-phenylpropan-2-yl]amino]-4-oxobutanoic acid).

The term "cyclamate" as used herein refers to the anion derived from sodium N-cyclohexylsulfamate.

The term "steviolate" as used herein refers to the anion derived from hydroxydehydrostevic acid.

The term "anion" is a type of ion and is included within the meaning of the term "ion." An "anion" is any molecule, portion of a molecule (e.g., Zwitterion), cluster of molecules, molecular complex, moiety, or atom that contains a net negative charge or that can be made to contain a net negative charge. The term "anion precursor" is used herein also refers to a molecule that can be converted to an anion via a chemical reaction (e.g., deprotonation).

The term "cation" is a type of ion and is included within the meaning of the term "ion." A "cation" is any molecule, portion of a molecule (e.g., Zwitterion), cluster of molecules, molecular complex, moiety, or atom, that contains a net positive charge or that can be made to contain a net positive charge. The term "cation precursor" is used herein also refers to a molecule that can be converted to a cation via a chemical reaction (e.g., protonation or alkylation).

The term "alkyl" as used herein refers to C1-16 inclusive, linear (i.e., "straight-chain"), branched, or cyclic, saturated or at least partially and, in some cases, fully unsaturated (i.e., alkenyl and alkynyl) hydrocarbon chains including, for example, methyl, ethyl, n-propyl, isopropyl, n-butyl, isobutyl, t-butyl, pentyl, hexyl, heptyl, octyl, nonyl, decyl, dodecyl, tetradecyl, hexadecyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a C1-8 alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to C1-16 straight-chain alkyls. In other embodiments, "alkyl" refers, in particular, to C1-16 branched-chain alkyls.

The term "ionic liquid" as used herein to refer to salts (i.e., compositions comprising cations and anions) that may be liquid. Since ionic liquid compositions are liquid, and thus not crystalline solids, at a given temperature, such compositions do not suffer from the problems of polymorphism associated with crystalline solids.

The term "liquid" as an ionic liquid refers to a generally amorphous, non-crystalline, or semi-crystalline state. For example, while some structured association and packing of cations and anions can occur at the atomic level, the disclosed ionic liquid compositions have minor amounts of such ordered structures and are therefore not crystalline solids. The compositions disclosed herein can be fluid and free-flowing liquids or amorphous solids such as glasses or waxes.

It is further understood, however, that the ionic liquid compositions of the disclosure can include solvent molecules (e.g., water, ethanol); however, these solvent molecules should not be present in excess in the sense that the disclosed ionic liquid compositions are dissolved in the solvent, forming a solution. That is, the disclosed ionic liquid compositions contain no or minimal amounts of solvent molecules that are free and not bound or associated with the ions present in the ionic liquid composition. Thus, the disclosed ionic liquid compositions can be liquid hydrates or solvates, but not solutions.

In addition to the cations and anions, the ionic liquid compositions disclosed herein can also contain nonionic species, such as solvents, preservatives, dyes, colorants, thickeners, surfactants, viscosity modifiers, mixtures and combinations thereof and the like. However, the amount of such nonionic species is typically low (e.g., less than about 10, 9, 8, 7, 6, 5, 4, 3, 2, or 1 wt. % based on the total weight of the composition). In some examples described herein, the disclosed ionic liquid compositions are neat; that is, the only materials present in the disclosed ionic liquids are the cations and anions that make up the ionic liquid compositions. It is understood, however, that with neat compositions, some additional materials or impurities can sometimes be present, albeit at low to trace amounts (e.g., less than about 10, 9, 8, 7, 6, 5, 4, 3, 2, or 1 wt. % based on the total weight of the composition).

The term "dietary supplement" as used herein is defined by the FDA as a product taken by mouth that contains a "dietary ingredient" intended to supplement the diet. The "dietary ingredients" in these products may include vitamins, minerals, herbs or other botanicals, amino acids, and substances such as enzymes, organ tissues, glandulars, and metabolites. Dietary supplements can also be extracts or concentrates, and may be found in many forms such as tablets, capsules, softgels, gelcaps, liquids, or powders. They can also be in other forms such as a bar, but if they are, information on their label must not represent the product as a conventional food or a sole item of a meal or diet.

Furthermore, dietary supplements of the present invention do not encompass pharmaceutical compositions, and the methods of the present invention do not encompass therapeutic treatments, unless specifically set forth in the claims as a pharmaceutical composition. While the embodiments described herein may utilize pharmaceutical grade ingredients for human consumption and other uses, the dietary supplements and associated approaches are non-pharmaceutical. The embodiments described herein are intended for use as dietary supplements only.

Dietary supplements for non-humans means a dietary supplement that is administered or taken by an individual more than once with the purpose of supplementing the diet to increase and/or maintain a component (e.g., creatine) of the supplement, or a substance comprising a component of the supplement (e.g., a creatine salt) in the body at a higher level(s) than that naturally occurring through natural or conventional meals. Additionally, dietary supplement further means an addition to the diet in a pill, capsule, tablet, powder, spread, jam, liquid form, and the like, which is not part of a natural or conventional food or food product, and which effectively increases the function of tissues when consumed. Dietary supplement may mean a feed supplement whereby a quantity of creatine is included in or added to feed given, typically as a quantity of creatine per amount of feed. In certain embodiments, the supplemented feed may have a predetermined amount of creatine per unit of feed (w/w, w/v, v/v, etc.). The predetermined amount of creatine may provide a desired dose of creatine per feeding. For example, certain livestock may be given a predetermined and/or approximate quantity of feed one or more times per day, week, month, etc. Creatine may be added to the feed to create a supplemented feed and/or fortified feed such that if the livestock consumes the provided feed the livestock will also consume the desired amount of creatine. The amount of supplemented feed for livestock, and thus the amount of creatine provided, may be determined based on the size and/or weight of the livestock. For purposes of this disclosure, a dose, a dosing, etc. may mean a quantity of supplemented feed provided to livestock.

The term "food additive" as used herein refers to a compound that is listed in the "Everything Added to Foods in the United States (EAFUS)" FDA database.

The term "fortify (food)" as used herein refers to a food additive intended to increase the nutritive value of food, especially with micronutrients.

The term "nutraceutical" as used herein refers to a food containing health-giving food additives or having medicinal benefit, including the prevention and treatment of disease such as, but not limited to, any condition that leads to muscle loss, including age-related muscle loss. Hence, compositions falling under the label "nutraceutical" may range from isolated nutrients, dietary supplements and specific diets to genetically engineered designer foods, herbal products, and processed foods such as cereals, soups and beverages. In a more technical sense, the term has been used to refer to a product isolated or purified from foods, and generally sold in medicinal forms not usually associated with food and demonstrated to have a physiological benefit or provide protection against chronic disease.

Since creatine is naturally occurring in, and can be extracted from, digestible foodstuff, the label "nutraceutical" may be applied. As used herein, the phrase "nutraceutically acceptable derivative" is used to refer to a derivative or substitute for the stated chemical species that operates in a similar manner to produce the intended effect, and is structurally similar and physiologically compatible, in the following discussion of the invention, it should be understood that the term "creatine" can refer to either the stated chemical species or to a nutraceutically acceptable derivative.

Compounds of the disclosure includes crystalline forms which may exist as mono-salts, poly-salts, and polymorphs. Solvates of the compounds formed with water or common organic solvents are also intended to be encompassed within the term. In addition, hydrate forms of the compounds and their salts are encompassed within this disclosure.

The term "solvate" as used herein refers to a physical association of a compound with one or more solvent molecules or a complex of variable stoichiometry formed by a solute (for example, a compound of the disclosure) and a solvent, for example, water, ethanol, or acetic acid. This physical association may involve varying degrees of ionic and covalent bonding, including hydrogen bonding. In certain instances, the solvate will be capable of isolation, for example, when one or more solvent molecules are incorporated in the crystal lattice of the crystalline solid. In general, the solvents selected do not interfere with the biological, activity of the solute. Solvates encompass both solution-phase and isolatable solvates. Representative solvates include hydrates, ethanolates, methanolates, and the like. Dehydrate, co-crystals, anhydrous, or amorphous forms of the compounds of the disclosure are also included. The term "hydrate" means a solvate wherein the solvent molecule(s) is/are $H_2O$, including, mono-, di-, and various poly-hydrates thereof. Solvates can be formed using various methods known in the art.

Description

Creatine is in high demand among athletes as the food supplement that facilitates muscle growth. Low palatability and bioavailability of naturally-occurring creatine has led to the development of a number of creatine-based salts. The present disclosure now provides a novel approach to the taste modulation of creatine, in which the creatine cation, or derivatives thereof, is coupled with anionic taste-modifiers such as, but not limited to, the sweeteners saccharinate, acesulfamate, or derivatives thereof, or the anion taurocholate, to form novel salts. The ionic conjugates synthesized using anion exchange techniques now have a more acceptable sweet taste for creatine saccharinate and creatine acesulfamate. Additionally, a change in bitterness for the creatine taurocholate compared to creatine has also been found. Saccharin, acesulfame, and taurocholate salts of a creatine alkyl ester were also synthesized and characterized.

The present disclosure provides embodiments of salts of creatine and creatine ethyl ester (CEE) wherein the anion is an artificial (non-saccharide) taste-modifier. The novel compounds represent stable white non-hygroscopic solids or semisolids that can readily dissolve in water and buffer solutions. Synthesis of novel creatine salts by the methods disclosed using environmentally safe solvents such as ethanol resulted in the formation of products in quantitative yields with sodium or potassium chloride as a byproduct. The creatine and creatine alkyl eater derivative salts are stable sweet-tasting compounds that are more palatable to a consumer than the parent creatine or derivatives thereof.

In the salts of the disclosure, saccharate, acesulfamate, and taurocholate are advantageous examples of useful anions. Saccharin and acesulfame represent highly sweet-tasting anions with acesulfame and saccharin being, respectively, 200 and 300 times sweeter than sucrose. Acesulfame and saccharin also have small molecular weights, 162 g/mol for acesulfame and 182 g/mol for saccharin. The taurocholate anion of salts 25 and 26 represents a dietary component important for achieving adequate levels of vitamins A and E in mammals (Sundaresan et al., (2005) *Int. J. Vitam. Nutr. Res.* 75: 133-1341). The novel salts of creatine 21a, 21b, 23a, 23b, 25, and 26 herein disclosed have reduced bitter taste, hygroscopicity, and low solubility problems exhibited by the original creatine monohydrate 3.

Dietary or food supplements are typically designed to compensate for insufficient or reduced levels of nutrients in the modern human diet. One particular goal in supplementing a diet is to increase or enhance the function of tissues such as muscle tissue. For example, in the sporting and athletic community, food supplements that specifically improve athletic ability are increasingly important since they can promote or enhance physical growth or endurance, or reduce recovery time after exertion. Older individuals may also use creatine salts of the disclosure to slow or prevent age-related muscle loss.

Increasing creatine levels in muscle through dietary supplementation has proven effective at enhancing athletic performance, increasing muscle workload and shortening muscle recovery time. In addition, there is increasing interest in creatine dietary supplements for a variety of therapeutic indications, including muscular dystrophy, cardiovascular diseases, neurodegenerative disorders, and mental retardation Accordingly, the creatine and creatine derivative salts of the disclosure may be advantageously incorporated into beverages such as, but not limited to, drinking waters, health beverages, energy drinks, mineral waters, alcoholic beverages, milk preparations, protein shakes, lactose-free drinks, and carbonated beverages, and the like; enteric-coated drug delivery systems, oral drug delivery systems, pharmaceutical capsules, pharmaceutical granules, pharmaceutical powders, pharmaceutical tablets.

Most advantageously, the salts of the disclosure can be provided as powders that are substantially in a dehydrated state or dry (lacking a moisture content). In such powders the salts are not substantially dissociated into cations and anions but may be solvates, including hydrates, and in crystalline form. The compositions of the disclosure, either dehydrated or moistened with, but not dissolved in, a liquid such as water, a buffer, an oil, or the like, may be admixed further with other nutrients, dietary supplements, pharmaceutically acceptable compounds, fillers, and the like for subsequent adding to a food or beverage or being consumed without further modification.

It is, however, further contemplated that the creatine salts of the present disclosure may be in the form of an ionic liquid as described in U.S. patent application U.S. Ser. No. 11/545,938.

This disclosure further encompasses, therefore, dietary supplement compositions that may be consumed alone, with a meal, or as a meal supplement. A dietary supplement composition provided herein can be taken with a meal or between meals. The ingredients of a dietary supplement composition as provided herein can work in conjunction with foods being consumed. In some cases, a dietary supplement composition provided herein can be included as a beverage alone or mixed with other dietary supplements. In some cases, a dietary supplement composition provided herein can be provided in a powdered form that can be combined with a liquid to form a beverage. For example, a package can include between 10 grams and 100 grams of a dry powered form of a dietary supplement composition provided herein and can be designed to be mixed with water (or another consumable liquid) to form a beverage. A beverage including a dietary supplement composition provided herein can be an aqueous solution or slurry.

The compositions as provided herein can be in the form of a liquid, solution, suspension, pill, capsule, tablet, gel cap, powder, or gel. Most advantageously, the compositions are provided as powders for dispensation into a liquid, onto a food or admixed with foods. For oral administration, tablets or capsules can be prepared by conventional means with acceptable excipients such as binding agents, fillers, lubricants, disintegrants, or wetting agents. The tablets can be coated, if desired. Liquid preparations for oral administration can take the form of, for example, solutions, syrups, or suspension, or they can be presented as a dry product for constitution with water or other suitable liquid vehicle before use. Dietary supplement compositions of the type described herein also can contain acceptable additives as will be understood by one skilled in the art depending on the particular form of the dietary composition. Non-limiting examples of such additives include suspending agents, emulsifying agents, non-aqueous vehicles, preservatives, buffer salts, flavoring, and coloring as appropriate.

In some cases, the dietary composition can be included as a supplement in a carrier food form, for example in the form of a shake, bar, or soup. For example, the creatine or creatine-derivative salts as herein provided can be incorporated into a base of such as soy crisps, syrups, sweeteners, and fiber sources to produce an extruded protein bar. The final product can be consumed as one serving as either a meal replacement or snack item.

In another example, a blend of ingredients provided herein can be added to a meal replacement shake base. The configuration of a suitable shake base is known in the art and will be apparent to one skilled in the art in view of the disclosure herein. Final serving size can be, for example, 30 g to be dispersed into 8 ounces of milk or water (or other suitable liquid) to form one complete serving. Final serving size can be greater or lesser than 30 grams (e.g., 15 or 60 grams) and can provide more or less than one complete serving (e.g., half a serving or two servings).

The salts of the creatine, or derivative thereof, of the disclosure can be incorporated in an amount of at least 0.1% by weight based on the total weight of the present composition, preferably ranging from about 5% to 95% by weight, and more preferably from about 10% to 50% by weight The composition may further include one or more ingredients for improving the palatability, stability, flavor or nutritive quality of the present compositions, in varying amounts, depending upon the effect desired. Such ingredients may include electrolytes, or may be selected from the group consisting of: vitamins, lipids, carbohydrates, amino acids, trace elements, colorings, flavors, natural health improving substances, anti-oxidants, stabilizers, preservatives, and buffers. The composition may be unflavored or where the ingredient is a recognized foodstuff (e.g. honey or syrup), the composition may have the normal flavor of the ingredient.

Examples of such ingredients include, but are not limited to, protein isolate, magnesium chloride, potassium citrate, calcium phosphate tribasic, soy lecithin, sodium citrate, choline chloride, ascorbic acid, taurine, L-carnitine, zinc sulfate, ferrous sulfate, alpha-tocopherol acetate, niacinamide, carrageenin, calcium pantothenate, manganese sulfate, thiamine chloride hydrochloride, pyridoxine hydrochloride, riboflavin, copper sulfate, vitamin A palmitate, folic acid, biotin, sodium molybdate, chromium chloride, potassium iodide, sodium selenate, phylloquinone, cyanocobalamin, vitamins A, thiamin ($B_1$), riboflavin ($B_2$), $B_6$, $B_{12}$, D, $D_2$, E and K, folic acid, niacin, choline, biotin, pantothenic acid and the like. The nutritional ingredients may be added in amounts ranging from about 20% to 100% of their recommended daily allowance (RDA).

Preservatives can be typically selected from sodium benzoate, potassium sorbate, methylparaben, propylparaben, and the like. The preservative is typically present in the composition in an amount of from about 0.1% to 0.6% by weight based on the total weight of the composition, preferably from about 0.30% to 0.45% by weight based on the total weight of the composition, and more preferably from about 0.15% to 0.30% by weight based on the total weight of the composition.

These compositions of the disclosure can be admixed in the formulation in a variety of manners. For example, where the formulation may include other ingredients as described below, the mixture can be admixed directly with those other ingredients, generally homogeneously throughout the formulations, in whatever physical form it may take. Of course, sometimes, the compositions can be premixed and added to other ingredients to produce the formulation.

The formulation, as mentioned above, can be included in dietary supplements. The supplements can be in the form of tablets, powders, gels, or liquids (a tablet, for the purposes of the present invention and as used throughout the application disclosure, refers to any form of a solid oral dosage, including but not limited to tablets, caplets, capsules, powders, etc.). The supplement can be formulated as a powder for mixing with consumable liquids such as milk, juice, water, or consumable gels or syrups for mixing into other dietary liquids or foods. The supplement also can be formulated with other foods or liquids to provide pre-measured supplemental foods, for example, single-serving bars. Flavors, excipients, binders, protein, complex carbohydrates, preservatives, chelating agents, and the like can be added depending on the application.

When implemented in a dietary supplement, the formulation can be administered in one or more tablets, administered twice a day. Of course, if desired, the dietary supplement can be administered in other forms and unit dosages as desired.

The dietary supplement can be formulated using any pharmaceutically acceptable form of other ingredients, for example, concentrates, phytochemicals, vitamins, minerals, and other nutrients, including salts and derivatives thereof. For example, suitable vitamins for use in the formulation and supplement can include vitamin A, vitamin B1, vitamin B2, vitamin B6, vitamin B12, niacin/niacinamide, pantothenic acid, folic acid, biotin, choline, vitamin C, vitamin D and vitamin E, optionally derived from plant and other natural sources. In addition to the vitamins listed above, minerals for use in the formulation and supplement can include boron, calcium, chromium, copper, iodine, magnesium, manganese, molybdenum, potassium, selenium, vanadium and zinc. Other vitamins and minerals may also be used.

The compounds and compositions of the disclosure may be provided as bulk preparations, most advantageously as powders, for dispensing to a liquid carrier, foodstuff, and the like. Packaging may be provided for maintaining the compositions in substantially dry powder form, for storage and transport, and may include such items as a scoop measure for delivering a predetermined amount of the composition for consumption by a human or animal.

One aspect of the disclosure, therefore, encompasses embodiments of a salt, or a solvate thereof, of creatine or a cationic derivative of creatine, and an anionic taste-modifier and can have the formula I:

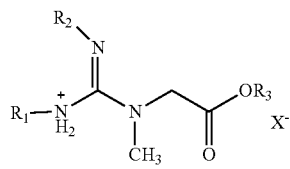

wherein $R_1$ and $R_2$ can each be independently an alkyl group or a hetaryl group and $R_3$ can be H or an alkyl group and X can be an anionic taste-modifier.

In some embodiments of this aspect of the disclosure, the creatine derivative can be a creatine alkyl ester cation.

In some embodiments of this aspect of the disclosure, R can be an alkyl group, or a monounsaturated alkyl having a $C_1$-$C_{16}$ chain.

In some embodiments of this aspect of the disclosure, R can be selected from the group consisting of a methyl group, an ethyl group, a propyl group, a butyl group, and a palmitoleate group.

In some embodiments of this aspect of the disclosure, the creatine alkyl ester cation can be a creatine ethyl ester (CEE) cation.

In some embodiments of this aspect of the disclosure, the anionic taste-modifier can be selected from the group consisting of: saccharinate, acesulfamate, taurocholate, neotamate, cyclamate, and steviolate, and anionic derivatives thereof.

In some embodiments of this aspect of the disclosure, the anionic taste-modifier can be a sweetener selected from saccharinate and acesulfamate.

In some embodiments of this aspect of the disclosure, the salt can be selected from the group consisting of:

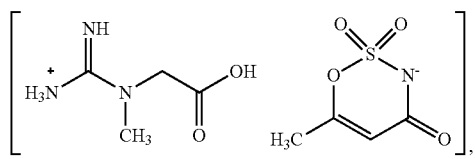
21a
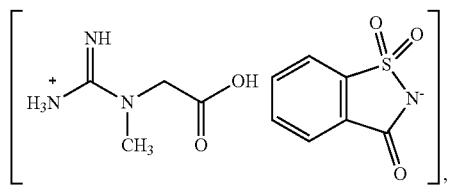
21b
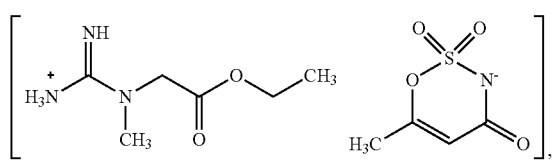
23a
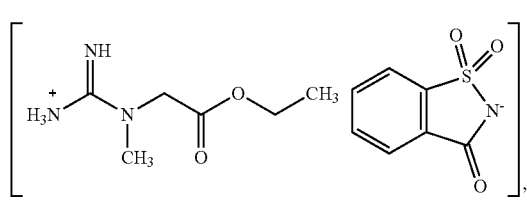
23b
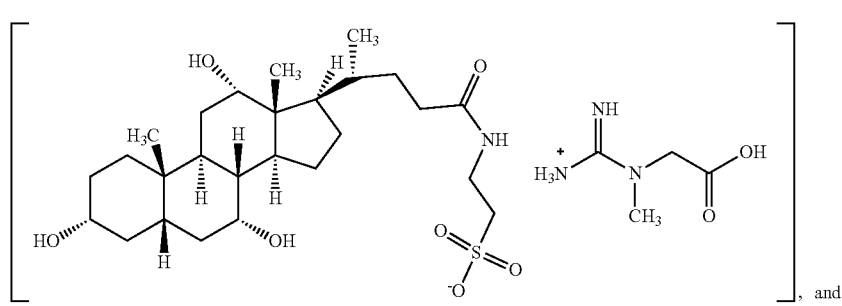
25
, and
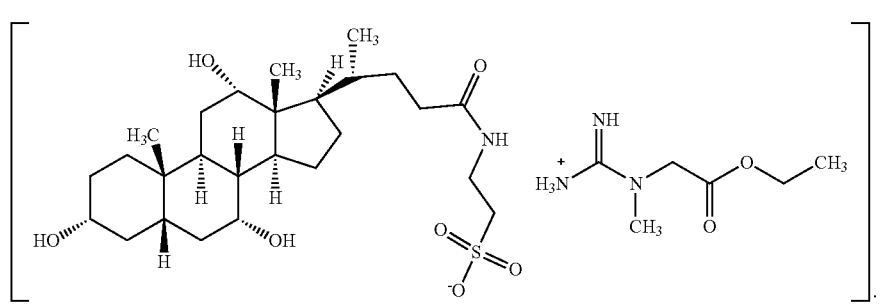
26

Another aspect of the disclosure encompasses embodiments of a composition comprising at least one mono- or poly-creatine salt or solvate thereof, wherein each salt or hydrate thereof consists of creatine or a cationic derivative of creatine, and an anionic taste-modifier and can have the formula I:

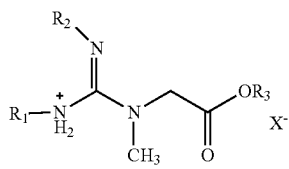

wherein $R_1$ and $R_2$ can each be independently an alkyl group or a hetaryl group and $R_3$ can be H or an alkyl group and X can be an anionic taste-modifier.

In some embodiments of this aspect of the disclosure, the creatine derivative can be a creatine alkyl ester cation.

In some embodiments of this aspect of the disclosure, R can be an alkyl group, or a monounsaturated alkyl having a $C_1$-$C_{16}$ chain.

In some embodiments of this aspect of the disclosure, R can be selected from the group consisting of a methyl group, an ethyl group, a propyl group, a butyl group, and a palmitoleate group.

In some embodiments of this aspect of the disclosure, the creatine alkyl ester cation can be a creatine ethyl ester (CEE) cation.

In some embodiments of this aspect of the disclosure, the anionic taste-modifier of each of the at least one of said salts can be selected from the group consisting of: saccharinate, acesulfamate, taurocholate, neotamate, cyclamate, and steviolate, and anionic derivatives thereof.

In some embodiments of this aspect of the disclosure, the anionic taste-modifier can be a sweetener selected from saccharinate and acesulfamate.

In some embodiments of this aspect of the disclosure, each of the at least one of said salts can be independently selected from the group consisting of:

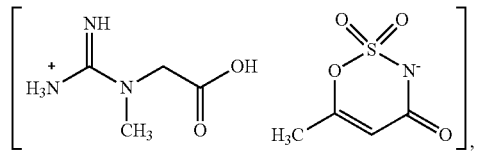

21a

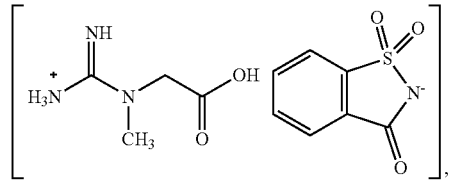

21b

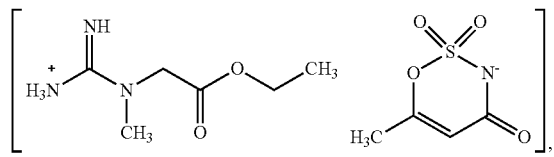

23a

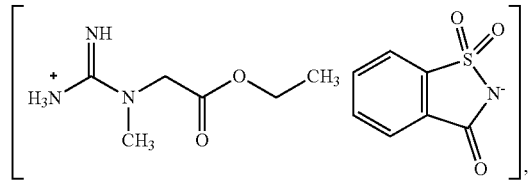

23b

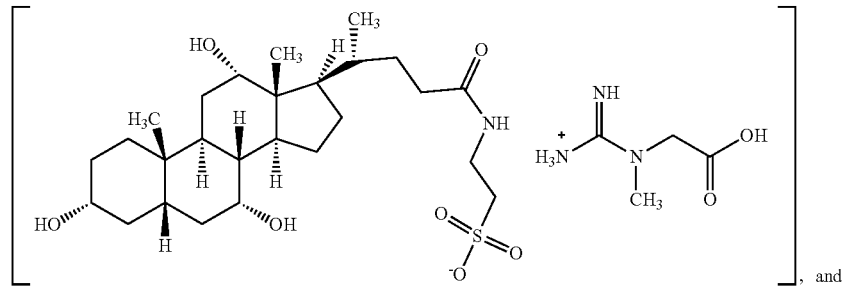

25

, and

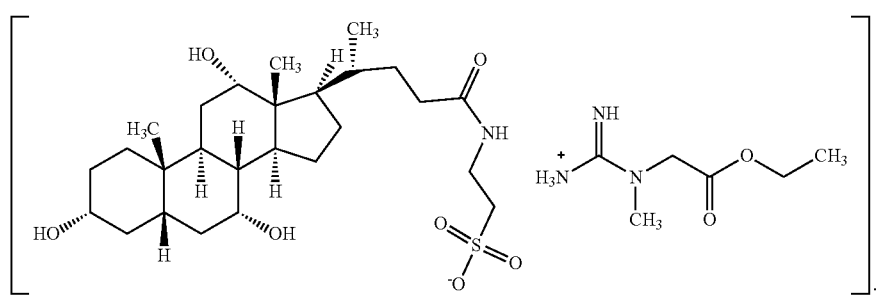

In some embodiments of this aspect of the disclosure, the composition can be a powder, an ionic liquid, or an oil.

In some embodiments of this aspect of the disclosure, the composition can further comprise an aqueous medium in an amount that does not result in dissociation of the creatine, or a cationic derivative of creatine, and the anionic taste-modifier. In some embodiments, the percent weight of the aqueous medium is from 0.001% to about 30%, from 0.001% to about 20%, 0.001% to about 10%, from 0.001% to about 5%, from 0.001% to about 2%, from 0.001% to about 1%, from 0.001% to about 0.5%, or from 0.001% to about 0.1%.

In some embodiments of this aspect of the disclosure, the creatine or a cationic derivative of creatine, and the anionic taste-modifier can be admixed with a non-aqueous medium.

In some embodiments of this aspect of the disclosure, the non-aqueous medium can be an edible oil or lipid.

In some embodiments of this aspect of the disclosure, the composition can be in a foodstuff or beverage formulated for consumption by a human or animal.

Still another aspect of the disclosure encompasses embodiments of a dietary supplement composition contained in a bulk package, wherein the dietary supplement composition is a powder, a non-aqueous oil, or a semi-solid, the bulk package containing the dietary supplement composition and, optionally, a measuring scoop sized to scoop an amount of the dietary supplement composition suitable for blending with a liquid to form a single serving of a beverage, the dietary supplement composition consisting essentially of at least one creatine salt or solvate thereof, wherein each salt or solvate thereof consists of creatine or a cationic derivative of creatine, and an anionic taste-modifier.

In some embodiments of this aspect of the disclosure, the cationic creatine derivative can be a creatine alkyl ester cation.

In some embodiments of this aspect of the disclosure, the creatine alkyl ester cation can be a creatine ethyl ester (CEE) cation.

In some embodiments of this aspect of the disclosure, the anionic taste-modifier of each of the at least one of said salts is selected from the group consisting of: saccharinate, acesulfamate, taurocholate, neotamate, cyclamate, and steviolate, and anionic derivatives thereof.

In some embodiments of this aspect of the disclosure, the anionic taste-modifier can be a sweetener selected from saccharinate and acesulfamate.

In some embodiments of this aspect of the disclosure, the at least one of said salts can be independently selected from the group consisting of:

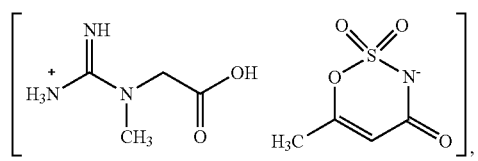

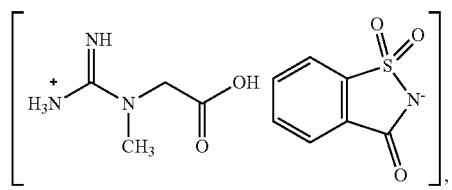

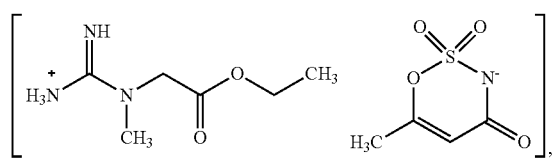

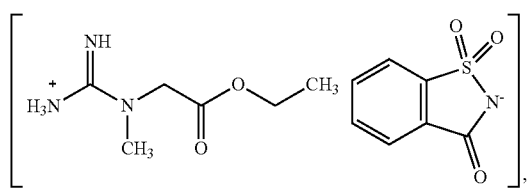

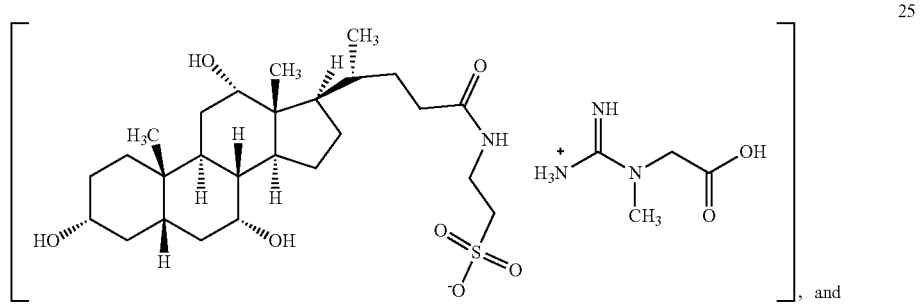

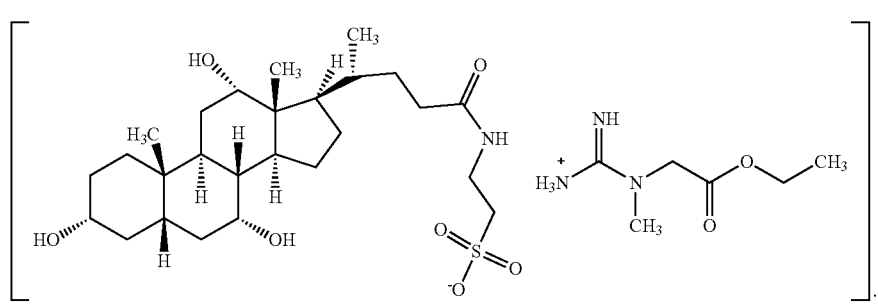

It should be emphasized that the embodiments of the present disclosure, particularly any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following claims.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified.

EXAMPLES

Example 1

Anion Exchange of Saccharin Sodium 2b and Acesulfame Potassium 2a Salts with Creatine Hydrochloride 1 and Creatine Ethyl Ester Hydrochloride 4:

Synthesis of creatine acelsulfamate 21a and creatine saccharinate 21b (Scheme 1) was carried out by stirring equimolar quantities of creatine hydrochloride 4 and potassium acesulfamate 20a or sodium saccharinate 20b in ethanol at 50° C. for 4 h. Sodium or potassium chloride was isolated with filtration. After solvent was evaporated, product was washed with ethyl ether leading to the formation of white semisolid product 21a and white solid 21b in 96% and 98% yields that were readily soluble in organic solvents and water.

Scheme 1
Synthesis of creatine acesulfamate 21a and creatine saccharinate 21b.

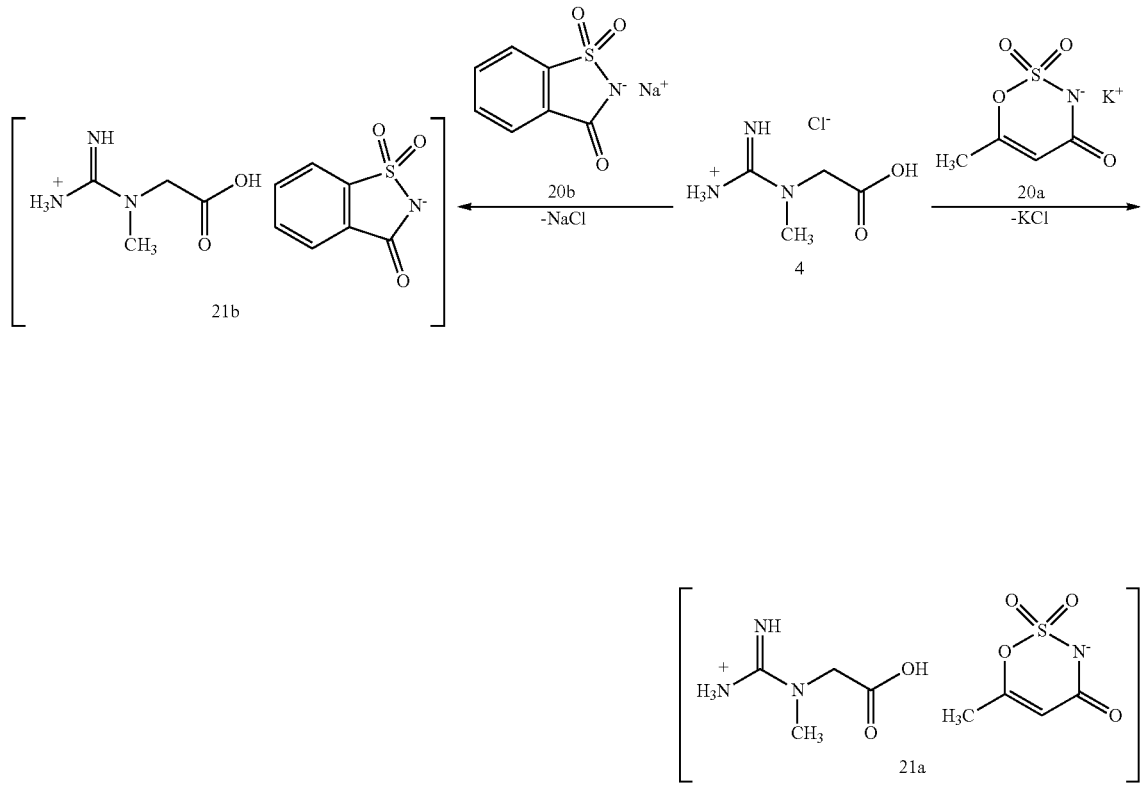

The $^1$H NMR in DMSO-$d_6$, creatine acesulfamate 21a revealed four protons of NH$_2$ and NH$_2^+$ groups as a broad singlet at 7.47 ppm. CH group of acesulfame was identified as a singlet at 5.47 ppm. A singlet at 4.16 was identified as a CH$_2$ group of creatine. Two singlets at 2.94 and 1.97 ppm correspond to the methyl groups of creatine and acesulfame. The $^{13}$C spectrum of 21a revealed three signals in the weak field that correspond to the two C=O and one C=NH$_2^+$ groups at 169.8, 169.2, and 162.3 ppm. The signal of a quaternary carbon of acesulfame was found at 158.1 ppm. CH signal of acesulfame was identified at 101.2 ppm. Signal for CH$_2$ group of creatine was found at 51.8 ppm. Methyl groups of creatine and acesulfame were identified as two signals at 37.6 and 20.0 ppm. HRMS data for 21a identified creatine residue at 132.0766 with the calculated weight of 132.0768 under positive ionization and acesulfame moiety was identified at 161.9868 with the calculated weight of 161.9867 at negative ionization mode.

The $^1$H NMR spectrum of creatine saccharinate 21b in DMSO-$d_6$ revealed a doublet for two protons, a multiplet for four protons and a singlet for two protons in the downfield area at 7.96, 7.86-7.80, and 7.52 ppm correspondingly. These signals refer to the four protons of NH$_2$ and NH$_2$+ groups and four protons of the aromatic rig of saccharin moiety. A singlet at 4.19 ppm was identified as CH$_2$ group of creatine. One singlet at 2.97 ppm was identified as a methyl group of creatine. The $^{13}$C spectrum of 21b revealed three signals in the weak field that correspond to the two C=O and one C=NH$_2$+ groups at 169.4, 164.0, and 157.7 ppm of creatine and saccharin. Six carbon atoms at the aromatic region of saccharin were identified at 142.1, 133.8, 133.6, 130.7, 124.0, and 120.5 ppm. The signal of CH$_2$ group of creatine was identified at 51.4 ppm and the signal for the methyl group of creatine was found at 37.4 ppm. HRMS data for 21b revealed creatine moiety at 132.0766 and saccharin moiety at 181.9916 with the positive and negative ionization modes.

Example 2

Synthesis of Creatine Ethyl Ester (CEE) Acelsulfamate 23a and Creatine Ethyl Ester (CEE) Saccharinate 23b:

Synthesis of creatine ethyl ester (CEE) acelsulfamate 23a and creatine ethyl ester (CEE) saccharinate 23b (Scheme 2) was carried out by stirring equimolar quantities of CEE hydrochloride 22 and potassium acesulfamate 20a or sodium saccharinate 20b in ethanol at 50° C. for 4 h. Sodium or potassium chloride was isolated from the reaction mixture with filtration. After solvent was evaporated, product was washed with ethyl ether leading to the formation of white solid products 23a and 23b that were readily soluble in organic solvents and water in 97%, and 96% respectively.

Scheme 2
Synthesis of creatine ethyl ester acesulfamate 23a and creatine ethyl ester saccharinate 23b.

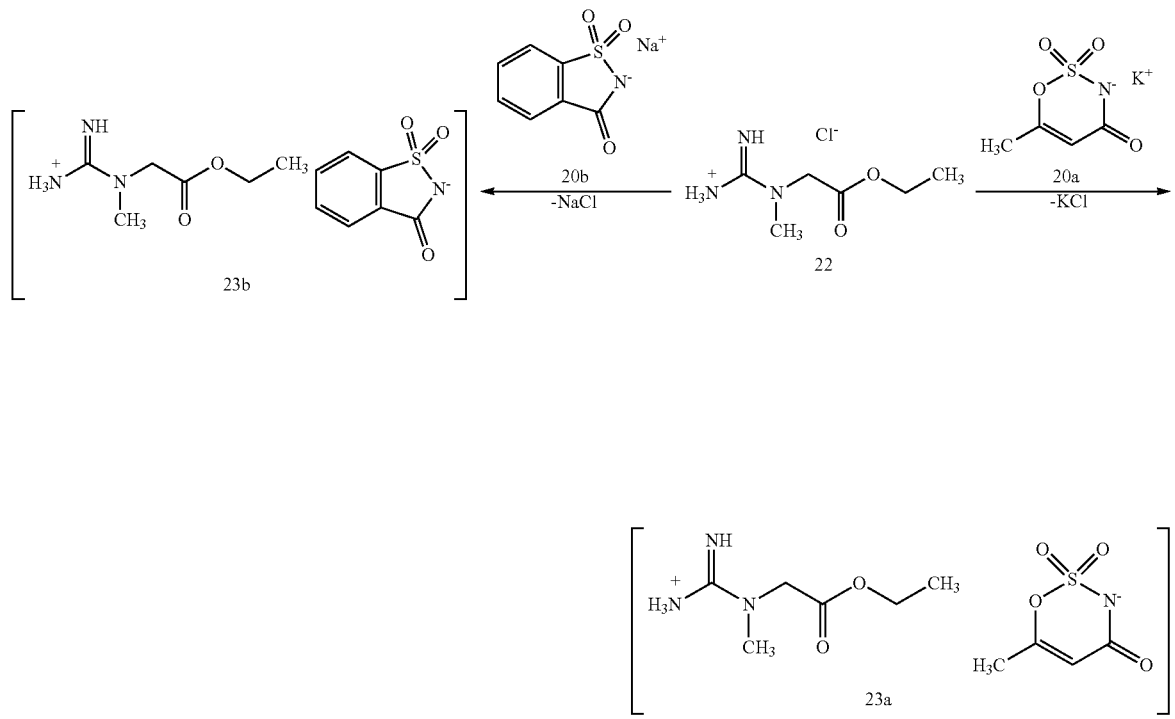

The $^1$H NMR of CEE acesulfame 23a in CD$_3$OD revealed signal of a CH group of acesulfame at 5.56 ppm. Multiplet signal of four protons of two CH$_2$ groups was identified around 4.30-4.24 ppm. Two singlet signals that correspond to methyl groups of creatine and acesulfame were identified at 3.11 and 2.09 ppm. A triplet signal of a methyl group of the creatine ester moiety was identified at 1.33 ppm. Signals of amino groups in the downfield region were not visible since CD$_3$OD was used as solvent. $^{13}$C spectrum of 23a revealed four signals in the weak field that correspond to two C=O, one quaternary carbon, and one C=NH$_2$+ groups at 173.2, 169.8, 164.4, and 160.0 ppm. Signal for the CH group of acesulfame was identified at 102.7 ppm. Signals for two CH$_2$ groups and three CH$_3$ groups of creatine and acesulfame were identified at 63.4, 53.1, 38.4, 20.3, and 14.9 ppm. HRMS data for 23a identified CEE residue at 160.1079 with the calculated weight of 160.1081 under positive ionization mode and acesulfame was identified at 161.9868 with the calculated weight of 161.9867 at negative ionization mode.

The $^1$H NMR spectrum of CEE saccharinate 23b in DMSO-d$_6$ revealed a multiplet for the NH$_2$ and NH$_2$$^+$ groups and the four aromatic protons of saccharin moiety. The CH$_2$ group for creatine was identified as a singlet at 4.44 ppm and the methylene group of the creatine ester moiety was identified as a multiplet at 4.32-4.28 ppm. NMe group of creatine was identified as a singlet at 3.12 ppm and the methyl group of creatine ester moiety was identified as a triplet at 1.36 ppm. $^{13}$C spectrum of 23b revealed three signals in the downfield that correspond to two C=O and one C=NH$_2$$^+$ groups at 172.5, 169.8, and 160.0 ppm of creatine and saccharin. Six carbon atoms at the aromatic region of saccharin were identified at 145.9, 135.3, 134.3, 133.9, 124.9, and 121.4 ppm. The signal of CH$_2$ group of creatine was identified at 53.1 ppm and the signal for the methyl group of creatine was wound at 38.4 ppm. Methylene group of creatine ester moiety was identified at 63.4 ppm and the methyl group of the ester moiety was found at 14.9 ppm. HRMS data for 23b revealed CEE moiety at 160.1080 and saccharin moiety at 181.9919 with the positive and negative ionization modes. Calculated molecular peak for CEE is 160.1081 and 181.9917 for saccharin.

Example 3

Anion Exchange of Sodium Taurocholate 24 with Creatine Hydrochloride 4 and Creatine Ethyl Ester Hydrochloride 22:

Synthesis of creatine taurocholate 25 and CEE taurocholate 26 (Scheme 3) was carried out by stirring equimolar quantities of creatine hydrochloride 4 or CEE hydrochloride 22 and sodium taurocholate 24 in ethanol in at 50° C. for 4 h. Sodium chloride then was then isolated with filtration. After solvent was evaporated, the product was washed with ethyl ether leading to the formation of white solid products 25 and 26 which were readily soluble in organic solvents and water. Taurocholate salts of creatine 25 and creatine ethyl ester 26 were isolated in 97% and 95% respectively.

Scheme 3
Synthesis of creatine taurocholate 25, and CEE taurocholate 26.

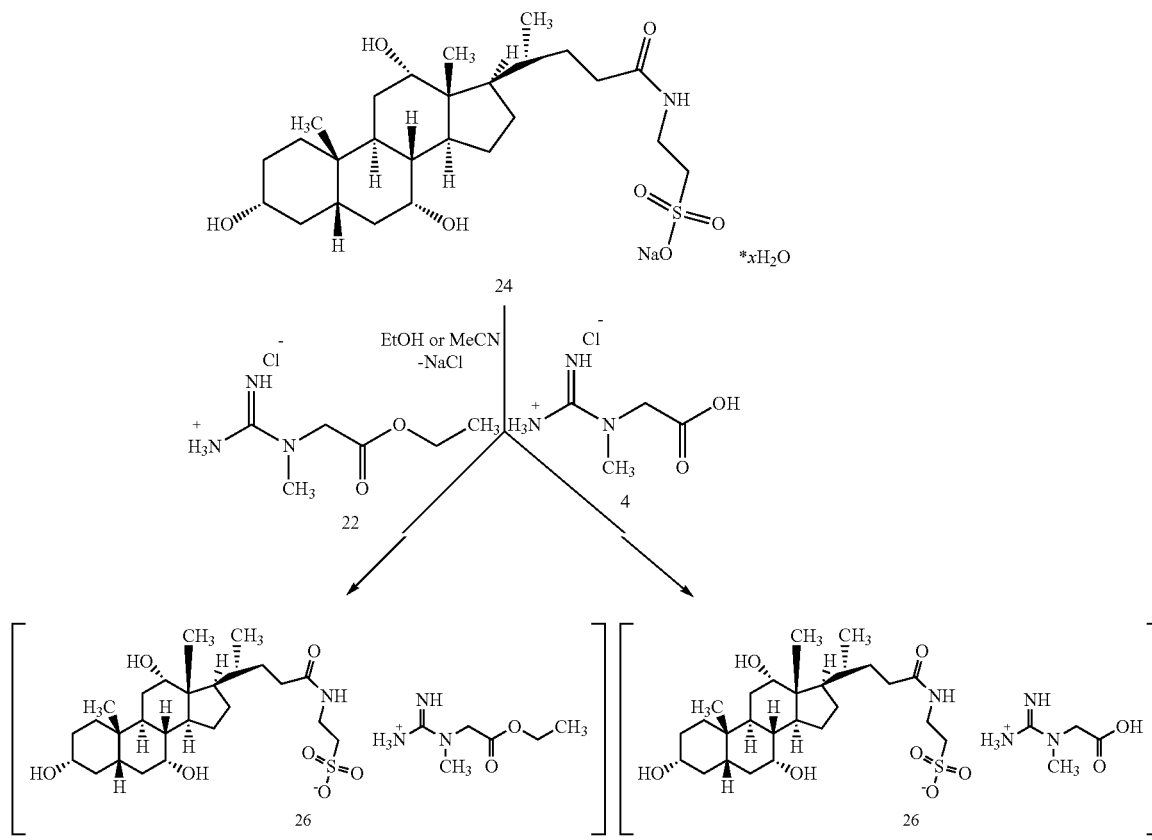

The ¹H NMR spectrum in CD₃OD, creatine taurocholate 25 revealed singlet, doublet, and multiplet signals that summed up into fifty two protons. Signals of protons from amide for taurocholate and amino groups for creatine were detected at 7.65 and 7.44 ppm respectively. Signal for the $CH_2$ group of creatine was detected at 4.15 ppm. Methyl groups for creatine and taurocholate were identified as a triplet at 1.05 ppm, a doublet at 0.91 ppm and two singlets at 0.80 ppm and 0.58 ppm. Most of the signals in the strong field referred to the proton signals of taurocholate moiety of the salt 25. ¹³C spectrum of 25 revealed three signals at 172.2, 169.3, and 157.5 ppm that corresponded to the C=O and $C=NH_2^+$ moieties of both taurocholine and creatine. Signals between 71.0 and 12.3 ppm corresponded to the C, CH, $CH_2$, and four signals of methyl groups for creatine and taurocholine moieties of 25. Molecular ion peaks for creatine and taurocholine were identified with HRMS at both positive and negative modes. Molecular weight for creatine was calculated as 132.0768 under positive ionization, and the peak at 132.0768 was identified as creatine moiety. Taurocholine peak was identified under negative ionization at 514.2832 with the calculated weight of 514.2844.

The ¹H spectrum of CEE taurocholate 26 in CD₃OD revealed signals of protons at aliphatic regions. Signals for five methyl groups of the salt (two groups for creatine and three methyl groups for taurocholine) were identified as possible groups as a multiplet at 1.82-1.71 ppm, part of the multiplet at 1.61-1.51 ppm, multiplet at 1.43-1.26 ppm, a singlet at 0.91 ppm, and a broad singlet at 0.71 ppm. Signals of amino groups or hydroxyl groups were not visible due to the use of CD₃OD as solvent. ¹³C spectrum of 26 revealed thirty two carbon signals. Two signals of C=O groups and one signal of a $C=NH_2+$ group were found at 177.0, 169.8, and 160.0 ppm. Signals between 74.5 and 13.5 ppm belonged to C, CH, $CH_2$, and $CH_3$ groups of creatine ethyl ester taurocholate 26. Molecular ions of CEE and taurocholine were identified with HRMS. Molecular weight for CEE was calculated as 160.1081, and the signal at 160.1080 was identified under positive ionization mode. Taurocholine moiety was identified under negative ionization with the molecular ion peak at 514.2830 with the calculated weight of 514.2844.

Example 4

Stability Study:

Mobile phase was 50% water and 50% acetonitrile with 0.1% formic acid in each. Column was a 2 mm×15 cm C18 column with 3 um particles. Flow rate 0.2 mL/min. Retention time was 1.7 min for creatine and 1.8 min for creatinine. The electrospray ion source was operated in positive mode and the MS was operated in MRM mode monitoring the following mass transitions: Creatine: 132>90; Creatinine: 114>86

Samples were dissolved in distilled water and kept at 20° C. Mass spectrometry used a Waters Premier XE triple quadrupole mass spectrometer. Liquid chromatography used a Waters Acquity UPLC system.

Table 1 below shows decomposition of creatine acesulfame 4 and creatine HCl 21a over 333 hours. Experiment was double checked with two simultaneous injections of each sample in various time intervals. At first, time intervals were 8 hours but since the decomposition was under 0.5% for 21a and 2.5% for 4, time intervals were increased. Formation of creatinine for both samples was minor and did not increase 3.6% for 4 and 1% for 21a, which shows stability of creatine samples in deionized water at room temperature for the period of time of 333 hours.

TABLE 1

Decomposition of creatine HCl 21a and creatine acesulfame 4 over time.

| Sample | Time (Hrs) | | | | | | | | |
|---|---|---|---|---|---|---|---|---|---|
| | 0 | 8 | 16 | 24 | 32 | 40 | 48 | 56 | 64 |
| Salt 4, % | 98.3 | 97.5 | 97.6 | 97.5 | 97.5 | 97.5 | 97.5 | 97.6 | 97.5 |
| Creatinine, % | 1.7 | 2.5 | 2.4 | 2.5 | 2.5 | 2.5 | 2.5 | 2.4 | 2.5 |
| Salt 4, % | 98.2 | 97.5 | 97.6 | 97.5 | 97.6 | 97.6 | 97.5 | 97.5 | 97.5 |
| Creatinine, % | 1.8 | 2.5 | 2.4 | 2.5 | 2.4 | 2.4 | 2.5 | 2.5 | 2.5 |
| Salt 21a, % | 99.6 | 99.6 | 99.6 | 99.5 | 99.5 | 99.5 | 99.5 | 99.5 | 99.5 |
| Creatinine, % | 0.4 | 0.4 | 0.4 | 0.5 | 0.5 | 0.5 | 0.5 | 0.5 | 0.5 |
| Salt 21a, % | 99.6 | 99.6 | 99.6 | 99.5 | 99.6 | 99.5 | 99.5 | 99.5 | 99.5 |
| Creatinine, % | 0.4 | 0.4 | 0.4 | 0.5 | 0.4 | 0.5 | 0.5 | 0.5 | 0.5 |

| Sample | Time (Hrs) | | | | | | | | |
|---|---|---|---|---|---|---|---|---|---|
| | 72 | 138 | 166 | 190 | 214 | 240 | 287 | 310 | 333 |
| Salt 4, % | 97.5 | 97.0 | 97.0 | 97.0 | 96.9 | 97.0 | 96.8 | 96.7 | 96.4 |
| Creatinine, % | 2.5 | 3.0 | 3.0 | 3.0 | 3.1 | 3.0 | 3.2 | 3.3 | 3.6 |
| Salt 4, % | 97.4 | 97.2 | 97.0 | 97.0 | 96.7 | 96.7 | 96.5 | 96.4 | 96.5 |
| Creatinine, % | 2.6 | 2.8 | 3.0 | 3.0 | 3.3 | 3.3 | 3.5 | 3.6 | 3.5 |
| Salt 21a, % | 99.5 | 99.4 | 99.3 | 99.3 | 99.2 | 99.2 | 99.1 | 99.1 | 99.0 |
| Creatinine, % | 0.5 | 0.6 | 0.7 | 0.7 | 0.8 | 0.8 | 0.9 | 0.9 | 1.0 |
| Salt 21a, % | 99.5 | 99.4 | 99.3 | 99.3 | 99.3 | 99.2 | 99.1 | 99.1 | 99.0 |
| Creatinine, % | 0.5 | 0.6 | 0.7 | 0.7 | 0.7 | 0.8 | 0.9 | 0.9 | 1.0 |

Example 5

Experimental:
$^1$H NMR spectra were recorded at 500 MHz and $^{13}$C NMR spectra were recorded at 125 MHz at room temperature. Chemical shifts are reported in ppm relative either to TMS as internal standard or to the residual solvent peak. The following abbreviations are used to describe spin multiplicity: s=singlet, d=doublet, t=triplet, q=quartet, m=multiplet, brs=broad singlet, dd=doublet of doublets. HRMS were recorded on a QTof-USA (Waters, Milford Mass) spectrometer operating in the ESI mode. Stability studies were run using the MS is a Waters Premier XE triple quadrupole mass spectrometer. The LC is a Waters Acquity UPLC system. All commercially available substrates and solvents were used as received without further purification.

Example 6

Synthesis of Creatine Acesulfamate 21a and Creatine Saccharinate 21b:
To the solution of creatine hydrochloride 1 (1.0 mmol, 168 mg) in EtOH (15 mL) equimolar quantity of sweetener salt (potassium 6-methyl-4-oxo-4H-1,2,3-oxathiazin-3-ide 2,2-dioxide 0.201 g for 20a and sodium benzo[d]isothiazol-2,2-dioxide 0.201 g for 20a and sodium benzo[d]isothiazol-3-olate 1,1-dioxide hydrate 0.205 g for 20b) was added and the mixture was then stirred for 4 h at the 50° C. Sodium or potassium chloride, formed during the reaction, was separated by filtration through the 22 micron membrane filter and the filtrate was taken to dryness. After that diethyl ether (3×25 mL) was added to product and it was evaporated to give products 21a,b in quantitative yields.

Creatine acesulfamate 21a: Amino((carboxymethyl)(methyl)amino)methaniminium 6-methyl-4-oxo-4H-1,2,3-oxathiazin-3-ide 2,2-dioxide

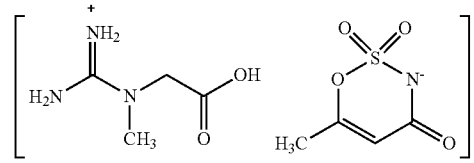

White semisolid (96%, 0.283 g, 0.96 mmol). $^1$H NMR (500 MHz, DMSO-d$_6$, δ) 7.47 (brs, 4H), 5.47 (s, 1H), 4.16 (s, 2H), 2.94 (s, 3H), 1.97 (s, 3H); $^{13}$C NMR (125 MHz, DMSO-d$_6$, δ) 169.8, 169.2, 162.3, 158.1, 101.2, 51.8, 37.6, 20.0. HRMS (ESI) calcd for C$_4$H$_{10}$N$_3$O$_2$ [M+H]$^+$ 132.0768, found 132.0766; HRMS (ESI) calcd for C$_4$H$_4$NO$_4$S [M−H]$^-$ 161.9867, found 161.9867.

Creatine saccharinate 21b: Amino((carboxymethyl)(methyl)amino)methaniminium 3-oxo-3H-benzo[d]isothiazol-2-ide 1,1-dioxide

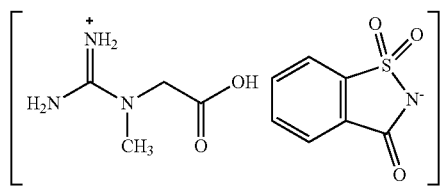

White solid (98%, 0.308 g, 0.98 mmol). M.p. 198.6-199.8° C.; $^1$H NMR (500 MHz, DMSO-d$_6$, δ) 7.96 (d, J=7.3 Hz, 2H), 7.86-7.80 (m, 4H) 7.52 (s, 2H), 4.19 (s, 2H), 2.97 (s, 3H); $^{13}$C NMR (125 MHz, DMSO-d$_6$, δ) 169.4, 164.0, 157.7, 142.1, 133.8, 133.6, 130.7, 124.0, 120.5, 51.4, 37.4. HRMS (ESI) calcd for C$_4$H$_{10}$N$_3$O$_2$ [M+H]$^+$ 132.0768, found 132.0766; HRMS (ESI) calcd for C$_7$H$_4$NO$_3$S [M−H]$^-$ 181.9917, found 181.9916.

Example 7

Synthesis of Creatine Ethyl Ester Acesulfamate 23a and Creatine Ethyl Ester Saccharinate 23b
To the solution of CEE hydrochloride 22 (1.0 mmol, 195 mg) in EtOH (15 mL) equimolar quantity of sweetener salt (potassium 6-methyl-4-oxo-4H-1,2,3-oxathiazin-3-ide 2,2-dioxide 0.201 g for 20a and sodium benzo[d]isothiazol-3-olate 1,1-dioxide hydrate 0.205 g for 20b) was added and the mixture was then stirred for 4 h at the 50° C. Sodium or potassium chloride, formed during the reaction, was separated by filtration through the 22 micron membrane filter and the filtrate was taken to dryness. Diethyl ether was added to the products and after it was evaporated, products 23a and 23b were isolated as white solids in quantitative yields.

Creatine ethyl ester acesulfamate 23a: Amino((2-ethoxy-2-oxoethyl)(methyl)amino)methaniminium 6-methyl-4-oxo-4H-1,2,3-oxathiazin-3-ide 2,2-dioxide

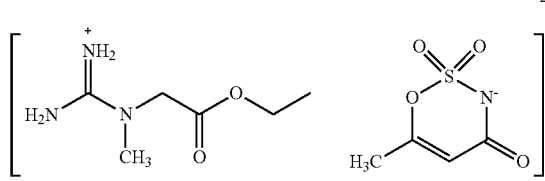

23a

White solid (97%, 0.312 g, 0.97 mmol). M.p. 118.9-122.0° C.; $^1$H NMR (500 MHz, CD$_3$OD, δ) 5.56 (s, 1H), 4.30-4.24 (m, 4H), 3.11 (s, 3H), 2.09 (s, 3H), 1.33 (t, J=7.2 Hz, 3H); $^{13}$C NMR (125 MHz, CD$_3$OD, δ) 173.2, 169.8, 164.4, 160.0, 102.7, 63.4, 53.1, 38.4, 20.3, 14.9. HRMS (ESI) calcd for C$_6$H$_{14}$N$_3$O$_2$ [M+H]$^+$ 160.1081, found 160.1079; HRMS (ESI) calcd for C$_4$H$_4$NO$_4$S [M−H]$^−$ 161.9867, found 161.9868.

Creatine ethyl ester saccharinate 23b: Amino((2-ethoxy-2-oxoethyl)(methyl)amino)methaniminium 3-oxo-3H-benzo[d]isothiazol-2-ide 1,1-dioxide

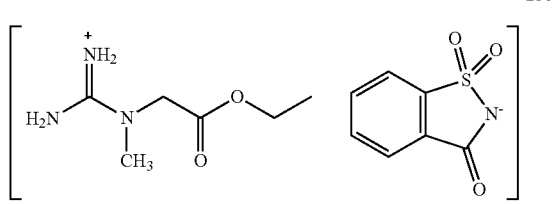

23b

White solid (96%, 0.329 g, 0.96 mmol). M.p. 183.9° C.; $^1$H NMR (500 MHz, DMSO-d$_6$, δ) 7.83-7.75 (m, 7H), 4.44 (s, 2H), 4.32-4.28 (m, 2H), 3.12 (s, 3H), 1.36 (t, J=7.1 Hz, 3H); $^{13}$C NMR (125 MHz, CD$_3$OD, δ) 172.5, 169.8, 160.0, 145.9, 135.3, 134.3, 133.9, 124.9, 121.4, 63.4, 53.1, 38.4, 14.9. HRMS (ESI) calcd for C$_6$H$_{14}$N$_3$O$_2$ [M+H]$^+$ 160.1081, found 160.1080; HRMS (ESI) calcd for C$_7$H$_4$NO$_3$S [M−H]$^−$ 181.9917, found 181.9919.

Example 8

Synthesis of Creatine Taurocholate 25:

To the solution of creatine hydrochloride 4 (1.0 mmol, 0.16 g) in EtOH (15 mL) equimolar quantity of sodium taurocholate hydrate 24 (1.0 mmol, 0.538 g) was added and the mixture was then stirred for 4 h at the 50° C. Sodium chloride, formed during the reaction, was separated by filtration through the 22 micron membrane filter and the filtrate was taken to dryness. Diethyl ether was added to the product and after it was evaporated, product 25 was isolated as white solid in quantitative yield.

Creatine taurocholate 25: Amino((carboxymethyl)(methyl)amino)methaniminium 2-((R)-4-((3R,5S,7R,8R,9S,10S,12S,13R,14S,17R)-3,7,12-trihydroxy-10,13-dimethylhexadecahydro-1H-cyclopenta[a]phenanthren-17-yl)pentanamido)ethane-1-sulfonate

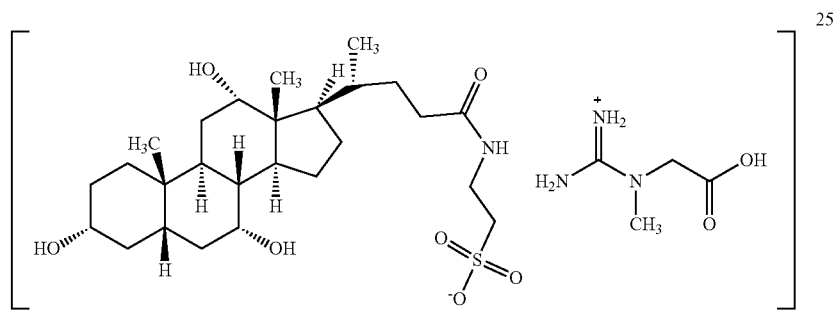

25

White solid (97%, 0.627 g, 0.97 mmol). M.p. 133.8-142.7; $^1$H NMR (500 MHz, DMSO-d$_6$, δ) 7.65 (t, J=5.4 Hz, 1H), 7.44 (br s, 4H), 4.34-4.29 (m, 2H), 4.15 (s, 2H), 4.08 (s, 1H), 3.98 (s, 1H), 3.79 (s, 1H), 3.61 (s, 1H), 3.43 (q, J=7.0 Hz, 2H), 3.30-3.16 (m, 3H), 2.94 (s, 3H), 2.53 (t, J=7.4 Hz, 2H), 2.23 (q, J=12.4 Hz, 1H), 2.17-2.11 (m, 1H), 2.08-2.03 (m, 1H), 2.00-1.89 (m, 2H), 1.81-1.72 (m, 3H), 1.66-1.61 (m, 3H), 1.46-1.39 (m, 2H), 1.39-1.31 (m, 2H), 1.31-1.20 (m, 2H), 1.20-1.10 (m, 1H), 1.05 (t, J=7.0 Hz, 3H), 0.91 (d, J=6.3 Hz, 3H), 0.80 (s, 3H), 0.58 (s, 3H); $^{13}$C NMR (125 MHz, DMSO-d$_6$, δ) 172.2, 169.3, 157.5, 71.0, 70.4, 66.2, 56.0, 51.3, 50.6, 46.1, 45.7, 41.5, 41.3, 37.1, 35.5, 35.3, 35.1, 34.9, 34.4, 32.7, 31.6, 28.5, 27.3, 26.2, 22.8, 22.6, 18.5, 17.1, 12.3. HRMS (ESI) calcd for C$_4$H$_{10}$N$_3$O$_2$ [M+H]$^+$ 132.0768, found 132.0768; HRMS (ESI) calcd for C$_{26}$H$_{44}$NO$_7$S [M−H]$^−$ 514.2844, found 514.2832.

Example 9

Synthesis of Creatine Ethyl Ester Taurocholate 26:

To the solution of CEE hydrochloride 22 (1.0 mmol, 0.195 g) in EtOH (15 mL) equimolar quantity of sodium taurocholate hydrate 24 (1.0 mmol, 0.538 g) was added and the mixture was then stirred for 4 h at the 50° C. Sodium chloride, formed during the reaction, was separated by filtration through the 22 micron membrane filter and filtrate was taken to dryness. Diethyl ether was added to the product and after evaporation, product 26 was isolated as white solid in quantitative yield.

Creatine ethyl ester taurocholate 26: Amino((2-ethoxy-2-oxoethyl)(methyl)amino)methaniminium 2-((R)-4-((3R,5S, 7R, 8R,9S,10S,12S,13R,14S, 17R)-3,7,12-trihydroxy-10,13-dimethylhexadecahydro-1H-cyclopenta[a]phenanthren-17-yl)pentanamido)ethane-1-sulfonate

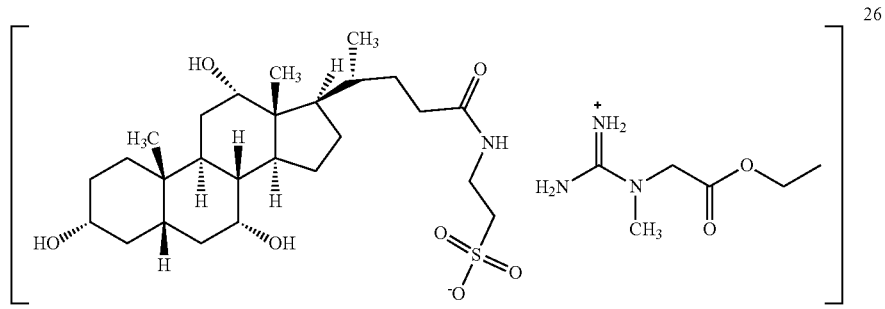

White solid (95%, 0.641 g, 0.95 mmol). M.p. 179.4-195.4° C.; $^1$H NMR (500 MHz, CD$_3$OD, δ) 4.27-4.23 (m, 1H), 4.19 (s, 1H), 3.95 (s, 1H), 3.79 (s, 1H), 3.58 (t, J=7.0 Hz, 2H), 3.49 (q, J=7.0 Hz, 1H), 3.40-3.35 (m, 2H), 3.19 (s, 2H), 3.07 (s, 1H), 2.96 (t, J=3.0 Hz, 2H), 2.31-2.23 (m, 3H), 2.14-2.07 (m, 1H), 2.02-1.92 (m, 2H), 1.90-1.83 (m, 2H), 1.82-1.71 (m, 3H), 1.67-1.61.4 (m, 1H), 1.61-1.51 (m, 5H), 1.43-1.26 (m, 6H), 1.17 (t, J=7.1, 2H), 1.12-1.09 (m, 1H), 1.03 (d, J=6.1 Hz, 2H), 0.98-0.95 (m, 2H), 0.91 (s, 3H), 0.71 (br s, 3H). $^{13}$C NMR (125 MHz, CD$_3$OD) δ 177.0, 169.8, 160.0, 74.5, 73.3, 69.5, 63.4, 58.8, 53.1, 52.0, 48.5, 48.0, 43.6, 43.5, 41.5, 40.9, 38.4, 37.4, 37.1, 36.4, 34.7, 33.6, 31.7, 30.1, 29.1, 28.3, 24.7, 23.7, 18.9, 18.3, 14.9, 13.5. HRMS (ESI) calcd for C$_6$H$_{14}$N$_3$O$_2$ [M+H]$^+$ 160.1081, found 160.1080; HRMS (ESI) calcd for C$_{26}$H$_{44}$NO$_7$S [M−H]$^−$ 514.2844, found 514.2830.

Example 10

Figure 3:
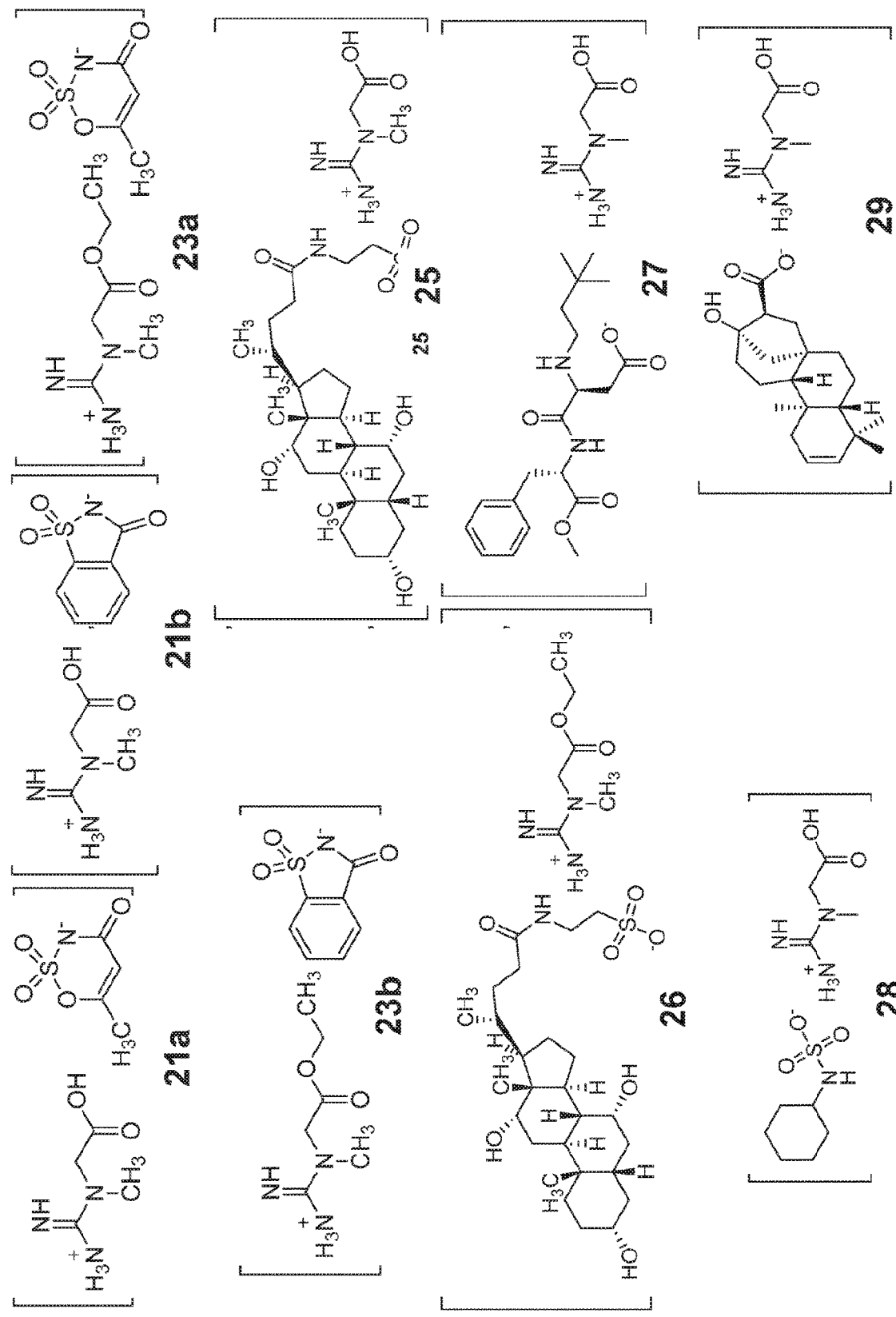
FIG. 3 illustrates examples of salts of creatine and taste-modifiers of the disclosure.

Examples of other embodiments of creatine-taste modifier salts are shown in FIG. 3 having formulas 27, 28, and 29:

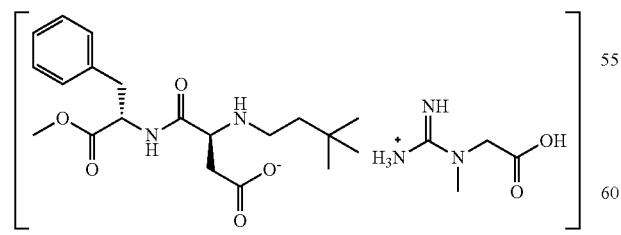

1-(carboxymethyl)-1-methylguanidinium (S)-3-((3,3-dimethylbutyl)amino)-4-(((S)-1-methoxy-1-oxo-3-phenylpropan-2-yl)amino)-4-oxobutanoate 27 (creatine neotamate)

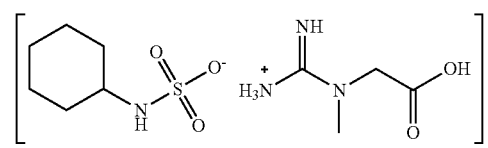

1-(carboxymethyl)-1-methylguanidinium cyclohexylsulfamate 28 (creatine cyclamate)

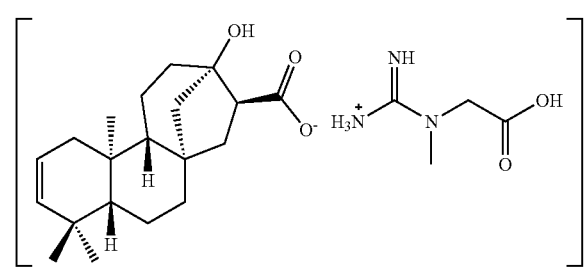

1-(carboxymethyl)-1-methylguanidinium (4aR,6aR,8S,9S, 11aR,11bS)-9-hydroxy-4,4,11b-trimethyl-1,4,4a,5,6,7,8, 9,10,11,11a,11b-dodecahydro-6a,9-methanocyclohepta [a]naphthalene-8-carboxylate (creatine steviolate).

We claim:
1. A creatine salt or a solvate thereof, comprising creatine or a cationic derivative of creatine and an anionic taste-modifier, the creatine salt having formula I:

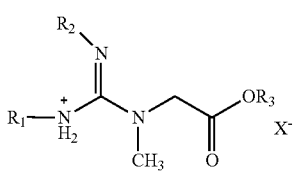

wherein:
R$_1$ and R$_2$ are each independently a hydrogen or an alkyl group;

R<sub>3</sub> is H or an alkyl group; and

X is selected from the group consisting of saccharinate, acesulfamate, neotamate, cyclamate, and steviolate.

2. The salt of claim 1, wherein cationic derivative of creatine is a creatine alkyl ester cation.

3. The salt of claim 1, wherein R$_3$ is an alkyl group.

4. The salt of claim 1, wherein R$_3$ is selected from the group consisting of a methyl group, an ethyl group, a propyl group, a butyl group, and a palmitoleate group.

5. The salt of claim 1, wherein the creatine alkyl ester cation is a creatine ethyl ester (CEE) cation.

6. The salt of claim 1, wherein the anionic taste-modifier is selected from the group consisting of saccharinate and acesulfamate.

7. The salt of claim 1, wherein said salt is selected from the group consisting of:

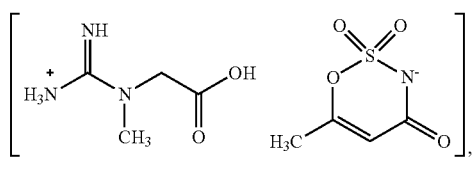

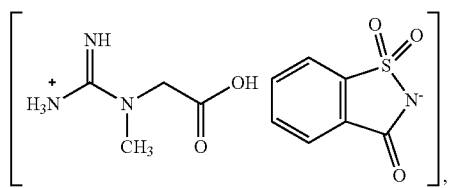

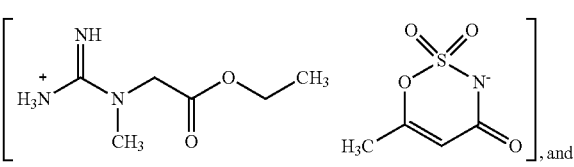

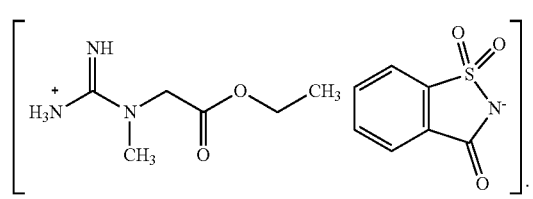

8. A composition comprising at least one creatine salt or solvate thereof, wherein each of the at least one creatine salt or solvate thereof comprises creatine or a cationic derivative of creatine and an anionic taste-modifier, the creatine salt having formula I:

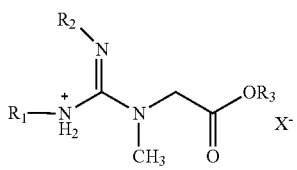

wherein:

R$_1$ and R$_2$ are each independently a hydrogen or an alkyl group;

R$_3$ is H or an alkyl group; and

X is selected from the group consisting of saccharinate, acesulfamate, neotamate, cyclamate, and steviolate.

9. The composition of claim 8, wherein the cationic derivative of creatine is a creatine alkyl ester cation.

10. The composition of claim 8, wherein R$_3$ can be an alkyl group.

11. The composition of claim 10, wherein R$_3$ is selected from the group consisting of a methyl group, an ethyl group, a propyl group, a butyl group, and a palmitoleate group.

12. The composition of claim 9, wherein the creatine alkyl ester cation is a creatine ethyl ester (CEE) cation.

13. The composition of claim 8, wherein the anionic taste-modifier is selected from the group consisting of saccharinate and acesulfamate.

14. The composition of claim 8, wherein each of the at least one of said salts is independently selected from the group consisting of:

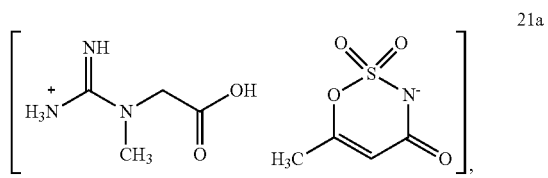

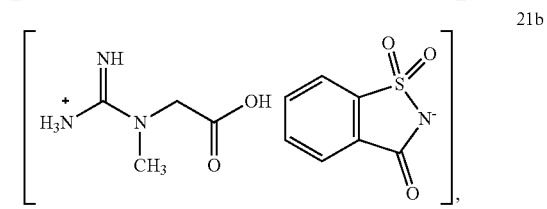

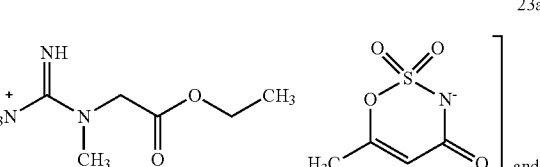

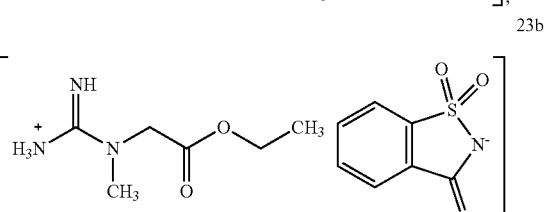

15. The composition of claim 8, wherein said composition is a powder, a non-aqueous oil, or a semi-solid.

16. The composition of claim 8, further comprising an aqueous medium in an amount that does not result in dissociation of the creatine or a cationic derivative of creatine, and the anionic taste-modifier.

17. The composition of claim 16, wherein the percent weight of the aqueous medium is from 0.001% to about 30%, from 0.001% to about 20%, 0.001% to about 10%, from 0.001% to about 5%, from 0.001% to about 2%, from 0.001% to about 1%, from 0.001% to about 0.5%, or from 0.001% to about 0.1%.

18. The composition of claim 8, wherein the creatine or cationic derivative of creatine, and the anionic taste-modifier are admixed with a non-aqueous medium.

19. The composition of claim 18, wherein the non-aqueous medium is an edible oil or lipid.

20. The composition of claim 8, wherein the composition is in a foodstuff or beverage formulated for consumption by a human or animal.

21. A dietary supplement composition contained in a bulk package,
wherein the dietary supplement composition is a powder, a non-aqueous oil, or a semi-solid,
optionally wherein the bulk package further comprises a measuring scoop sized to scoop an amount of the dietary supplement composition suitable for blending with a liquid to form a single serving of a beverage,
wherein the dietary supplement composition consisting essentially of at least one creatine salt or solvate thereof of claim 1.

22. The dietary supplement composition contained in the bulk package of claim 21, wherein the cationic derivative of creatine is a creatine alkyl ester cation.

23. The dietary supplement composition contained in the bulk package of claim 22, wherein the creatine alkyl ester cation is a creatine ethyl ester (CEE) cation.

24. The dietary supplement composition contained in the bulk package of claim 21, wherein the anionic taste-modifier is selected from the group consisting of saccharinate and acesulfamate.

25. The dietary supplement composition contained in the bulk package of claim 21, wherein each of the at least one said salts is independently selected from the group consisting of:

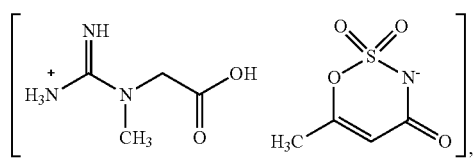
21a

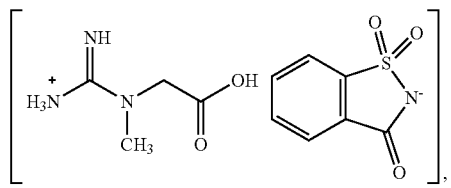
21b

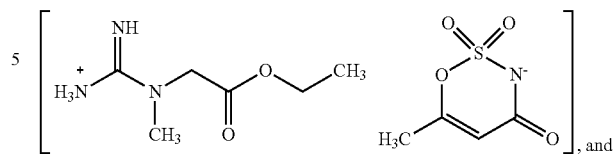
23a

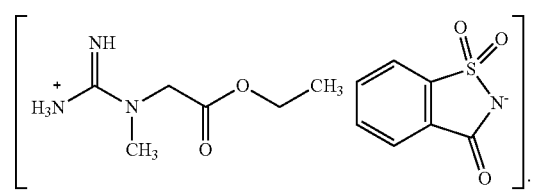
23b

26. The salt of claim 1, wherein said salt is

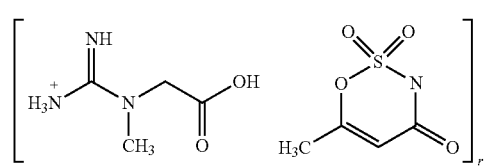
21a

27. A creatine salt or a solvate thereof, comprising creatine or a cationic derivative of creatine and an anionic taste-modifier, the creatine salt having formula I:

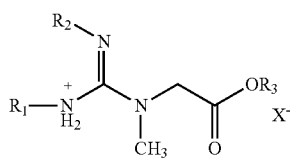

wherein:
R$_1$ and R$_2$ are each independently a hydrogen, an alkyl group, or a hetaryl group;
R$_3$ is H or an alkyl group;
X is taurocholate; and
wherein the creatine salt has a reduced bitter taste compared to creatine.

28. The salt of claim 27, wherein said salt is selected from the group consisting of:

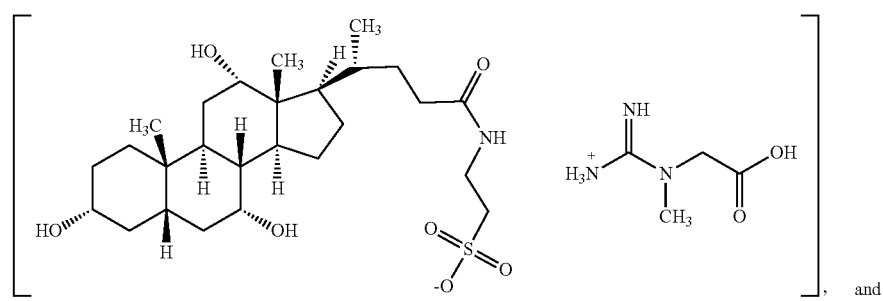
25

, and

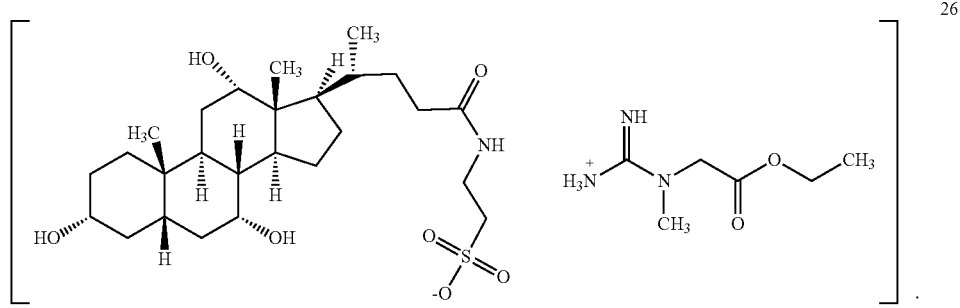
* * * * *